(12) United States Patent
Liu

(10) Patent No.: US 6,251,364 B1
(45) Date of Patent: *Jun. 26, 2001

(54) TERNARY LIGAND COMPLEXES USEFUL AS RADIOPHARMACEUTICALS

(75) Inventor: Shuang Liu, Chelmsford, MA (US)

(73) Assignee: DuPont Pharmaceuticals Company, Wilmington, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/277,936

(22) Filed: Mar. 29, 1999

(51) Int. Cl.$^7$ ............... A61K 51/00; C07F 5/00
(52) U.S. Cl. ............ 424/1.69; 424/1.65; 534/14
(58) Field of Search ............. 424/1.69, 1.65, 424/1.41, 1.49, 1.53, 1.73; 534/14, 10; 530/391.3, 317; 514/9, 11

(56) References Cited

U.S. PATENT DOCUMENTS 5,206,370  4/1993  Schwartz .................. 546/281

FOREIGN PATENT DOCUMENTS

| 0441953 | 8/1990 | (EP) | ............... | A61K/51/00 |
|---|---|---|---|---|
| 0569243 | 4/1993 | (EP) | ............... | C07F/13/00 |
| 9733627 | 9/1997 | (WO) | ............... | A61K/51/08 |

OTHER PUBLICATIONS

Hom et al, J.A. Nucl. Med. Biol. 1997, 24, p. 485.
M.K. Dewanjee, Semin. Nucl. Med. 1990, 20, p. 5.
Jurisson et al., Chem. Rev. 1993, 93, p. 1137.
Dilworth et al., S.J. Chem. Soc. Rev. 1998, 27, p. 43.
Liu et al., Bioconj. Chem. 1997, 8 p. 621.
Liu et al., Pure & Appl. Chem. 1991, 63, p. 427.
Griffiths et al., Bioconj. Chem. 1992, 3, p. 91.

*Primary Examiner*—Diana Dudash
*Assistant Examiner*—Michael G. Hartley
(74) *Attorney, Agent, or Firm*—Peter L. Dolan

(57) ABSTRACT

This invention relates to novel radiopharmaceuticals comprised of highly functionalized pyridine ligated technetium-99m labeled HYNIC-biomolecules that selectively localize at sites of disease and thus allow an image to be obtained of the loci using gamma scintigraphy. The invention also provides methods of use of the radiopharmaceuticals as imaging agents for the diagnosis of cardiovascular disorders such as thromboembolic disease or atherosclerosis, infectious disease and cancer.

10 Claims, No Drawings

TERNARY LIGAND COMPLEXES USEFUL AS RADIOPHARMACEUTICALS

FIELD OF THE INVENTION

This invention relates to novel radiopharmaceuticals which are useful as imaging agents for the diagnosis of cardiovascular disorders such as thromboembolic disease or atherosclerosis, infectious disease and cancer and kits containing the same. The radiopharmaceuticals are comprised of highly functionalized pyridine ligated technetium-99m labeled HYNIC-biomolecules that selectively localize at sites of disease and thus allow an image to be obtained of the loci using gamma scintigraphy. The invention also provides methods of use of the radiopharmaceuticals as imaging agents for the diagnosis of cardiovascular disorders such as thromboembolic disease or atherosclerosis, infectious disease and cancer.

BACKGROUND OF THE INVENTION

Radiopharmaceuticals are drugs containing a radionuclide, and are used routinely in nuclear medicine department for the diagnosis or therapy of various diseases. They are mostly small organic or inorganic compounds with definite composition. They can also be macromolecules such as antibodies and antibody fragments that are not stoichiometrically labeled with a radionuclide. Radiopharmaceuticals form the chemical basis for nuclear medicine, a group of techniques used for diagnosis and therapy of various diseases. The in vivo diagnostic information is obtained by intravenous injection of the radiopharmaceutical and determining its biodistribution using a gamma camera. The biodistribution of the radiopharmaceutical depends on the physical and chemical properties of the radiopharmaceutical and can be used to obtain information about the presence, progression, and the state of disease.

Radiopharmaceuticals can be divided into two primary classes: those whose biodistribution is determined exclusively by their chemical and physical properties; and those whose ultimate distribution is determined by their receptor binding or other biological interactions. The latter class is often called target-specific radiopharmaceuticals.

In general, a target specific radiopharmaceutical can be divided into four parts: a targeting molecule, a linker, a Bifunctional Chelator (BFC), and a radionuclide. The targeting molecule serves as a vehicle which carries the radionuclide to the receptor site at the diseased tissue. The targeting molecules can be macromolecules such as antibodies. They can also be small biomolecules (BM): peptides, peptidomimetics, and non-peptide receptor ligands. The choice of biomolecule depends upon the targeted disease or disease state. The radionuclide is the radiation source. The selection of radionuclide depends on the intended medical use (diagnostic or therapeutic) of the radiopharmaceutical. Between the targeting molecule and the radionuclide is the BFC, which binds strongly to the metal ion via several coordination bonds and is covalently attached to the targeting molecule either directly or through a linker. Selection of a BFC is largely determined by the nature and oxidation state of the metallic radionuclide. The linker can be a simple hydrocarbon chain or a long poly (ethylene glycol) (PEG), which is often used for modification of pharmacokinetics. Sometimes, a metabolizeable linker is used to increase the blood clearance and to reduce the background activity, thereby improving the target-to-background ratio.

The use of metallic radionuclides offers many opportunities for designing new radiopharmaceuticals by modifying the coordination environment around the metal with a variety of chelators. The coordination chemistry of the metallic radionuclide will determine the geometry of the metal chelate and the solution stability of the radiopharmaceutical. Different metallic radionuclides have different coordination chemistries, and require BFCs with different donor atoms and ligand frameworks. For "metal essential" radiopharmaceuticals, the biodistribution is exclusively determined by the physical properties of the metal chelate. For target-specific radiopharmaceuticals, the "metal tag" is not totally innocent because the target uptake and biodistribution will be affected by the metal chelate, the linker, and the targeting biomolecule. This is especially true for radiopharmaceuticals based on small molecules such as peptides due to the fact that in many cases the metal chelate contributes greatly to the overall size and molecular weight. Therefore, the design and selection of the BFC is very important for the development of a new radiopharmaceutical.

A BFC can be divided into three parts: a binding unit, a conjugation group, and a spacer (if necessary). An ideal BFC is that which is able to form a stable $^{99m}$Tc complex in high yield at very low concentration of the BFC-BM conjugate. There are several requirements for an ideal BFC. First, the binding unit can selectively stabilize an intermediate or lower oxidation state of Tc so that the $^{99m}$Tc complex is not subject to redox reactions; oxidation state changes are often accompanied by transchelation of $^{99m}$Tc from a $^{99m}$Tc-BFC-BM complex to the native chelating ligands in biological systems. Secondly, the BFC forms a $^{99m}$Tc complex which has thermodynamic stability and kinetic inertness with respect to dissociation. Thirdly, the BFC forms a $^{99m}$Tc complex with a minimum number of isomers since different isomeric forms of the $^{99m}$Tc-chelate may have significant impact on the biological characteristics of the $^{99m}$Tc-BFC-BM complex. Finally, the conjugation group can be easily attached to the biomolecule.

In simple technetium complex radiopharmaceuticals such as $^{99m}$Tc-sestamibi, [$^{99m}$Tc(MIBI)$_6$]$^+$ (MIBI=2-methoxy-2-methylpropyl-isonitrile) and $^{99m}$Tc-bicisate, [$^{99m}$TcO (ECD)] (ECD=1,1-ethylene dicysteine diethyl ester), the ligand (MIBI or ECD) is always present in large excess. The main factor influencing the $^{99m}$Tc-labeling kinetics is the nature of the donor atoms and the radiolabeling conditions. For receptor-based target specific radiopharmaceuticals, however, the use of large amount of BFCA-BM may result in receptor site saturation, blocking the docking of the $^{99m}$Tc-labeled BFC-BM, as well as unwanted side effects. In order to avoid these problems, the concentration of the BFC-BM in the radipharmaceutical kit has to be very low ($10^{-6}$–$10^{-5}$ M). Otherwise, a post-labeling purification is often needed to remove excess unlabeled BFC-BM, which is time consuming and thus not amenable for clinical use. Compared to the total technetium concentration (~$5\times10^{-7}$ M) in 100 mCi of [$^{99m}$Tc]pertechnetate (24 h prior-elution), the BFC-BM is not in overwhelmingly excess. Therefore, the BFC attached to the biomolecule must have very high radiolabeling efficiency in order to achieve high specific activity, the amount of unlabeled BFC-BM conjugate used to synthesize the radiopharmaceutical. Various BFCs have been used for the $^{99m}$Tc-labeling of biomolecules, and have been extensively reviewed (Hom, R. K. and Katzenellenbogen, J. A. *Nucl. Med. Biol.* 1997, 24, 485; Dewanjee, M. K. *Semin. Nucl. Med.* 1990, 20, 5; Jurisson, et al Chem. Rev. 1993, 93, 1137; Dilworth, J. R. and Parrott, S. J. *Chem. Soc. Rev.* 1998, 27, 43; Liu, et al Bioconj. Chem. 1997, 8, 621; Liu, et al *Pure & Appl. Chem.* 1991, 63, 427; Griffiths, et al *Bioconj. Chem.* 1992, 3, 91).

The use of hydrazines and hydrazides as BFCs to modify proteins for labeling with radionuclides has been recently disclosed in Schwartz et al U.S. Pat. No. 5,206,370. For labeling with technetium-99m, the hydrazino-modified protein is reacted with a reduced technetium species, formed by reacting pertechnetate with a reducing agent in the presence of a chelating dioxygen ligand. The technetium is bonded through what are believed to be hydrazino or diazenido linkages with the coordination sphere completed by the coligands such as glucoheptonate and lactate. Bridger et al European Patent Application No. 93302712.0 discloses a series of functionalized aminocarboxylates and their use for the radiolabeling of hydrazino-modified proteins. The improvements are manifested by shorter reaction times and higher specific activities for the radiolabeled protein. The best example is tricine.

Archer et al, European Patent application 90914225.9 discloses a series of technetium-99m complexes having a ternary ligand system comprised of a hydrazino or diazenido ligand, a phosphine ligand and a halide, in which the substituents on the hydrazido or diazenido ligand and those phosphine ligand can be independently varied. This disclosure does not teach or suggest how to achieve the superior control of biological properties that will result from a ternary ligand system in which the substituents on the three types of ligands can be independently varied. In addition, the radiopharmaceuticals described by Archer et al are formed in low specific activity. Therefore, there remains a need for new ternary ligand systems which form radiopharmaceuticals with high specific activity.

In WO 97/33627 the synthesis of novel radiolabeled platelet glycoprotein IIb/IIIa receptor antagonists as imaging agents for thromboembolic disorders is disclosed. Hydrazinonicotinamide (HYNIC) is used as the BFC for the modification of cyclic compounds while an aminocarboxylate such as tricine and an imine-N containing heterocycle are coligands. The combination of HYNIC-BM, tricine and a monodentate imine-N containing heterocycle produces a unique and versatile ternary ligand system that forms ternary ligand technetium complexes [$^{99m}$Tc(HYNIC-BM)(tricine)(heterocycle)] with high solution stability and only two detectable isomeric forms (due to chiral substituents on HYNIC).

The coligand has profound impact on the hydrophilicity and biological properties of the ternary ligand technetium complex [$^{99m}$Tc(HYNIC-BM) (tricine)(heterocycle)]. Thus, it is desirable to discover new coligands.

SUMMARY OF THE INVENTION

The present invention provides novel ternary technetium-99m radiopharmaceuticals composed of HYNIC-modified biomolecules, including IIb/IIIa antagonists, and vitronectin receptor antagonists, aminocarboxylates and highly functionalized pyridine derivatives. These radiopharmaceuticals are formed as minimal number of isomers, the relative ratio of which do not change with time. This invention provides novel radiopharmaceuticals and methods of using the same as imaging agents for the diagnosis of cardiovascular disorders such as thromboembolic disease or atherosclerosis, infectious disease and cancer. The radiopharmaceutical are comprised of highly functionalized pyridine ligated technetium-99m labeled HYNIC-biomolecules that selectively localize at sites of disease and thus allow an image to be obtained of the loci using gamma scintigraphy. The present invention further provides kits for the preparation of the radiopharmaceuticals.

The highly functionalized pyridine derivatives contain ester, polyester or polyhydroxy functionalities. These functionalities are of great interest because they can form neutral technetium-99m complexes (if there is no charge on the biomolecule), which can cross the cell membrane and potentially bind intracellular receptors. Once inside the cell, hydrolysis of one or more ester groups forms a negatively charged $^{99m}$Tc-species, which can not be easily diffused out from the cell. In this way, the target cell uptake may be significantly improved. On the other hand, if the ester group is hydrolyzed in the blood, the negatively charged $^{99m}$Tc-species is expected to have faster and more renal clearance. Therefore, the introduction of the ester groups has two potential advantages: increase in target cell uptake and decrease in background.

DETAILED DESCRIPTION OF THE INVENTION

[1] Thus, in an embodiment, the present invention provides a novel radiopharmaceutical of the formula (1):

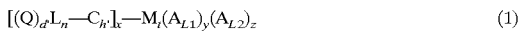

$$[(Q)_{d'}L_n-C_{h'}]_x-M_t(A_{L1})_y(A_{L2})_z \qquad (1)$$

and pharmaceutically acceptable salts thereof wherein,
Q is a biologically active group;
d' is 1 to 20;
$L_n$ is a linking group of formula:

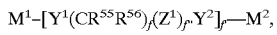

$$M^1-[Y^1(CR^{55}R^{56})_f(Z^1)_{f'}Y^2]_{f''}-M^2,$$

$M^1$ is $-[(CH_2)_g Z^1]_{g'}-(CR^{55}R^{56})_{g''}-$;
$M^2$ is $-(CR^{55}R^{56})_{g''}-[Z^1(CH_2)_g]_{g'}-$;
g is independently 0–10;
g' is independently 0–1;
g" is independently 0–10;
f is independently 0–10;
f' is independently 0–10;
f" is independently 0–1;
$Y^1$ and $Y^2$, at each occurrence, are independently selected from: a bond, O, $NR^{56}$, C=O, C(=O)O, OC(=O)O, C(=O)NH—, C=$NR^{56}$, S, SO, $SO_2$, $SO_3$, NHC(=O), $(NH)_2C$(=O), and $(NH)_2C$=S;
$Z^1$ is independently selected at each occurrence from a $C_6-C_{14}$ saturated, partially saturated, or aromatic carbocyclic ring system, substituted with 0–4 $R^{57}$; and a heterocyclic ring system, optionally substituted with 0–4 $R^{57}$;
$R^{55}$ and $R^{56}$ are independently selected at each occurrence from: H, $C_1-C_{10}$ alkyl substituted with 0–5 $R^{57}$, and alkaryl wherein the aryl is substituted with 0–5 $R^{57}$; $R^{57}$ is independently selected at each occurrence from the group: H, OH, $NHR^{58}$, C(=O)$R^{58}$, OC(=O)$R^{58}$, OC(=O)O$R^{58}$, C(=O)O$R^{58}$, C(=O)N$R^{58}$, —CN, S$R^{58}$, SO$R^{58}$, $SO_2R^{58}$, NHC(=O)$R^{58}$, NHC(=O)NH$R^{58}$, and NHC(=S)NH$R^{58}$, alternatively, when attached to an additional molecule Q,
$R^{57}$ is independently selected at each occurrence from the group: O, $NR^{58}$, C=O, C(=O)O, OC(=O)O, C(=O)N, C=$NR^{58}$, S, SO, $SO_2$, $SO_3$, NHC(=O), $(NH)_2C$(=O), and $(NH)_2C$=S;
$R^{58}$ is independently selected at each occurrence from the group: H, $C_1-C_6$ alkyl, benzyl, and phenyl;
x, y and z are independently 1 or 2;
$M_t$ is a transition metal radionuclide selected from the group: $^{99m}$TC, $^{186}$Re and $^{188}$Re;
$C_{h'}$ is a radionuclide metal chelator coordinated to transition metal radionuclide $M_t$, and is independently selected at each occurrence, from the group: $R^{40}N\!=\!N^+\!=$, $R^{40}R^{41}N\!-\!N\!=$, and $R^{40}N\!=\!N(H)\!-\!$;

$R^{40}$ is independently selected at each occurrence from the group: a bond to $L_n$, $C_1$–$C_{10}$ alkyl substituted with 0–3 $R^{52}$, aryl substituted with 0–3 $R^{52}$, cycloaklyl substituted with 0–3 $R^{52}$, heterocycle substituted with 0–3 $R^{52}$, heterocycloalkyl substituted with 0–3 $R^{52}$, aralkyl substituted with 0–3 $R^{52}$ and alkaryl substituted with 0–3 $R^{52}$;

$R^{41}$ is independently selected from the group: H, aryl substituted with 0–3 $R^{52}$, $C_1$–$C_{10}$ alkyl substituted with 0–3 $R^{52}$, and a heterocycle substituted with 0–3 $R^{52}$;

$R^{52}$ is independently selected at each occurrence from the group: a bond to $L_n$, =O, F, Cl, Br, I, —$CF_3$, —CN, —$CO_2R^{53}$, —C(=O)$R^{53}$, —C(=O)N($R^{53}$)$_2$, —CHO, —$CH_2OR^{53}$, —OC(=O)$R^{53}$, OC(=O)O$R^{53a}$, —O$R^{53}$, —OC(=O)N($R^{53}$)$_2$, —$NR^{53}$C(=O)$R^{53}$, —$NR^{53}$$_3$+, —$NR^{54}$C(=O)O$R^{53a}$, —$NR^{53}$C(=O)N($R^{53}$)$_2$, —$NR^{54}SO_2N(R^{53})_2$, —$NR^{54}SO_2R^{53a}$, —$SO_3H$, —$SO_2R^{53a}$, —$SR^{53}$, —S(=O)$R^{53a}$, —$SO_2N(R^{53})_2$, —N($R^{53}$)$_2$, —NHC(=NH)NH$R^{53}$, —C(=NH)NH$R^{53}$, =NO$R^{53}$, $NO_2$, —C(=O)NHO$R^{53}$, —C(=O)NHN$R^{53}R^{53a}$, —$OCH_2CO_2H$, and 2-(1-morpholino)ethoxy;

$R^{53}$, $R^{53a}$, and $R^{54}$ are each independently selected at each occurrence from the group: H, $C_1$–$C_6$ alkyl, and a bond to $L_n$;

$A_{L1}$ is a first ancillary ligand and is a dioxygen ligand or a functionalized aminocarboxylate;

$A_{L2}$ is second ancillary ligand, capable of stabilizing the radiopharmaceutical, of the formula:

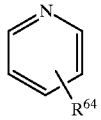

$R^{64}$ is selected from the group C(O)$R^{64a}$, C(O)N$R^{67}R^{64a}$, and C(O)O$R^{64a}$;

$R^{64a}$ is selected from the group: $C_{1-10}$ alkyl substituted with 1–5 $R^{65}$ and 0–2 $R^{65a}$, $C_{2-10}$ alkenyl substituted with 1–5 $R^{65}$ and 0–2 $R^{65a}$, $C_{2-10}$ alkynyl substituted with 1–5 $R^{65}$ and 0–2 $R^{65a}$, aryl substituted with 1–3 $R^{65}$ and 0–2 $R^{65a}$, and C3-10 carbocycle substituted with 1–3 $R^{65}$ and 0–2 $R^{65a}$;

$R^{65}$ is independently selected at each occurrence from the group: —O$R^{66}$, —$CO_2R^{66}$, —OC(=O)$R^{66}$, —OC(=O)O$R^{66}$, —$OCH_2CO_2R^{66}$, —$NR^{67}C(=O)$ O$R^{66}$, —$SO_2R^{66a}$, —$NR^{67}SO_2R^{66a}$, and —$PO_3R^{66a}$;

$R^{65a}$ is independently selected at each occurrence from the group: =O, F, Cl, Br, I, —$CF_3$, —CN, —$NO_2$, —C(=O)$R^{66}$, —C(=O)N($R^{66}$)$_2$, —N($R^{66}$)$_3$+, —OC(=O)N($R^{66}$)$_2$, —$NR^{66}C(=O)R^{66}$, —$NR^{67}C(=O)OR^{66a}$, —$NR^{66}C(=O)N(R^{66})_2$, —$NR^{67}SO_2N(R^{66})_2$, —$SO_2N(R^{66})_2$, and —N($R^{66}$)$_2$;

$R^{66}$ is independently selected at each occurrence from the group: H and $C_1$–$C_6$ alkyl;

$R^{66a}$ is independently selected at each occurrence from the group: H and $C_1$–$C_6$ alkyl; and, $R^{67}$ is independently selected at each occurrence from the group: H and $C_1$–$C_6$ alkyl.

[2] In a preferred embodiment, the present invention provides a novel radiopharmaceutical of formula (1), wherein:

Q is a biologically active molecule selected from the group: IIb/IIIa receptor antagonists, IIb/IIIa receptor ligands, fibrin binding peptides, leukocyte binding peptides, chemotactic peptides, somatostatin analogs, selectin binding peptides, and vitronectin receptor antagonists;

d' is 1 to 3;

$L_n$ is:

—(CR$^{55}$R$^{56}$)$_{g''}$—[Y$^1$(CR$^{55}$R$^{56}$)$_f$Y$^2$]$_{f'}$—(CR$^{55}$R$^{56}$)$_{g''}$—, g" is 0–5;

f is 0–5;

f' is 1–5;

$Y^1$ and $Y^2$, at each occurrence, are independently selected from: O, NR56, C=O, C(=O)O, OC(=O)O, C(=O)NH, C=N$R^{56}$, S, SO, $SO_2$, $SO_3$, NHC(=O), (NH)$_2$C(=O), and (NH)$_2$C=S;

$R^{55}$ and $R^{56}$ are independently selected at each occurrence from: H, $C_1$–$C_{10}$ alkyl and alkaryl;

x and y are 1;

$M_t$ is $^{99m}$Tc;

$C_{h'}$ is $R^{40}N\!=\!N^+\!=$ or $R^{40}R^{41}N\!-\!N\!=$;

$R^{40}$ is independently selected at each occurrence from the group: aryl substituted with 0–3 $R^{52}$, and heterocycle substituted with 0–3 $R^{52}$;

$R^{41}$ is independently selected from the group: H, aryl substituted with 0–1 $R^{52}$, $C_1$–$C_3$ alkyl substituted with 0–1 $R^{52}$, and a heterocycle substituted with 0–1 $R^{52}$;

$R^{52}$ is independently selected at each occurrence from the group: a bond to $L_n$, —$CO_2R^{53}$, —$CH_2OR^{53}$, —$SO_3H$, —$SO_2R^{53a}$, —N($R^{53}$)$_2$, —N($R^{53}$)$_3$+, —NHC(=NH)NH$R^{53}$, and —$OCH_2CO_2H$;

$R^{53}$ and $R^{53a}$ are each independently selected at each occurrence from the group: H and $C_1$–$C_3$ alkyl;

$A_{L1}$ is a functionalized aminocarboxylate;

$A_{L2}$ is second ancillary ligand, capable of stabilizing the radiopharmaceutical, of the formula:

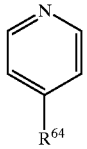

$R^{64}$ is selected from the group C(O)$R^{64a}$ and C(O)N$R^{67}R^{64a}$;

$R^{64a}$ is selected from the group: $C_{1-6}$ alkyl substituted with 1–5 $R^{65}$ and 0–2 $R^{65a}$, $C_{2-6}$ alkenyl substituted with 1–5 $R^{65}$ and 0–2 $R^{65a}$, and phenyl substituted with 1–3 $R^{65}$ and 0–2 $R^{65a}$;

$R^{65}$ is independently selected at each occurrence from the group: —O$R^{66}$, —$CO_2R^{66}$, —OC(=O)$R^{66}$, —OC(=O)O$R^{66}$, —$OCH_2CO_2R^{66}$, —$NR^{67}C(=O)OR^{66}$, —$SO_2R^{66a}$, —$NR^{67}SO_2R^{66a}$, and —$PO_3R^{66a}$;

$R^{65a}$ is independently selected at each occurrence from the group: =O, F, Cl, Br, I, —$CF_3$, —CN, —$NO_2$, —C(=O)$R^{66}$, —C(=O)N($R^{66}$)$_2$, —$NR^{66}C(=O)R^{66}$, —$SO_2N(R^{66})_2$, and —N($R^{66}$)$_2$;

$R^{66}$ is independently selected at each occurrence from the group: H and $C_1$–$C_6$ alkyl;

$R^{66a}$ is independently selected at each occurrence from the group: H and $C_1$–$C_6$ alkyl; and, $R^{67}$ is independently selected at each occurrence from the group: H and $C_1$–$C_6$ alkyl.

[3] In a more preferred embodiment, the present invention provides a novel radiopharmaceutical of formula (1), wherein:

Q is a biologically active molecule selected from the group: IIb/IIIa receptor antagonists and chemotactic peptides;

d' is 1;

$Y^1$ and $Y^2$, at each occurrence, are independently selected from: O, $NR^{56}$, C=O, C(=O)O, C(=O)O, C(=O)NH, C=$NR^{56}$, NHC(=O), and $(NH)_2C$(=O);

$R^{55}$ and $R^{56}$ are H;

z is 1;

$R^{40}$ is heterocycle substituted with $R^{52}$;

$R^{41}$ is H;

$R^{52}$ is a bond to $L_n$;

$A_{L1}$ is tricine;

$A_{L2}$ is second ancillary ligand, capable of stabilizing the radiopharmaceutical, of the formula:

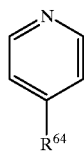

$R^{64}$ is selected from the group $C(O)R^{64a}$ and $C(O)NR^{67}R^{64a}$;

$R^{64a}$ is $C_{1-6}$ alkyl substituted with 1–5 $R^{65}$ and 0–2 $R^{65a}$;

$R^{65}$ is independently selected at each occurrence from the group: —$OR^{66}$, and —$CO_2R^{66}$;

$R^{65a}$ is independently selected at each occurrence from the group: =O, F, Cl, Br, I, —C(=O)$R^{66}$, —C(=O)N$(R^{66})_2$, —$NR^{66}$C(=O)$R^{66}$, and —N$(R^{66})_2$;

$R^{66}$ is independently selected at each occurrence from the group: H and $C_{1-3}$ alkyl;

$R^{66a}$ is independently selected at each occurrence from the group: H and $C_{1-3}$ alkyl; and, $R^{67}$ is independently selected at each occurrence from the group: H and $C_{1-3}$ alkyl.

[4] In an even more preferred embodiment, the present invention provides a novel radiopharmaceutical of formula (1), wherein:

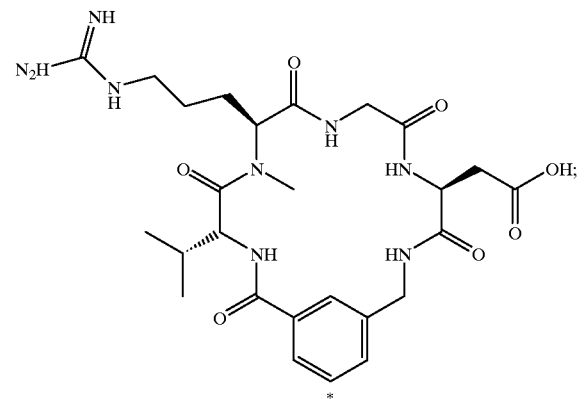

Q is d' is 1;

$L_n$ is attached to Q at the carbon atom designated with a * and has the formula:

—(C=O)NH(CH$_2$)$_5$C(=O)NH—;

$C_{h'}$ is

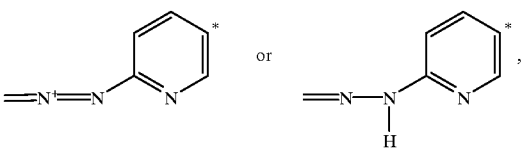

and is attached to $L_n$ at the carbon atom designated with a *;

$M_t$ is $^{99m}$Tc;

$A_{L1}$ is tricine;

and $A_{L2}$ is selected from the group:

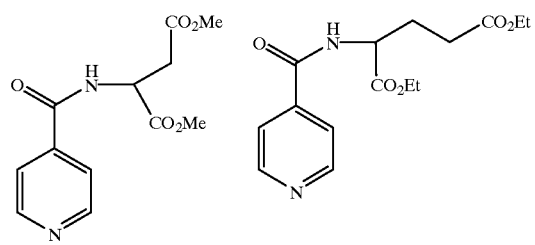

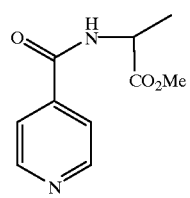

and

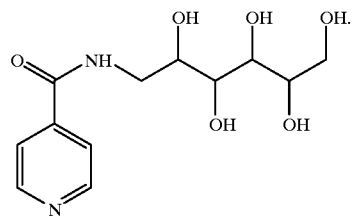

[5] In another preferred embodiment, the present invention provides a novel radiopharmaceutical of formula (1), wherein the radiopharmaceutical is selected from the group:

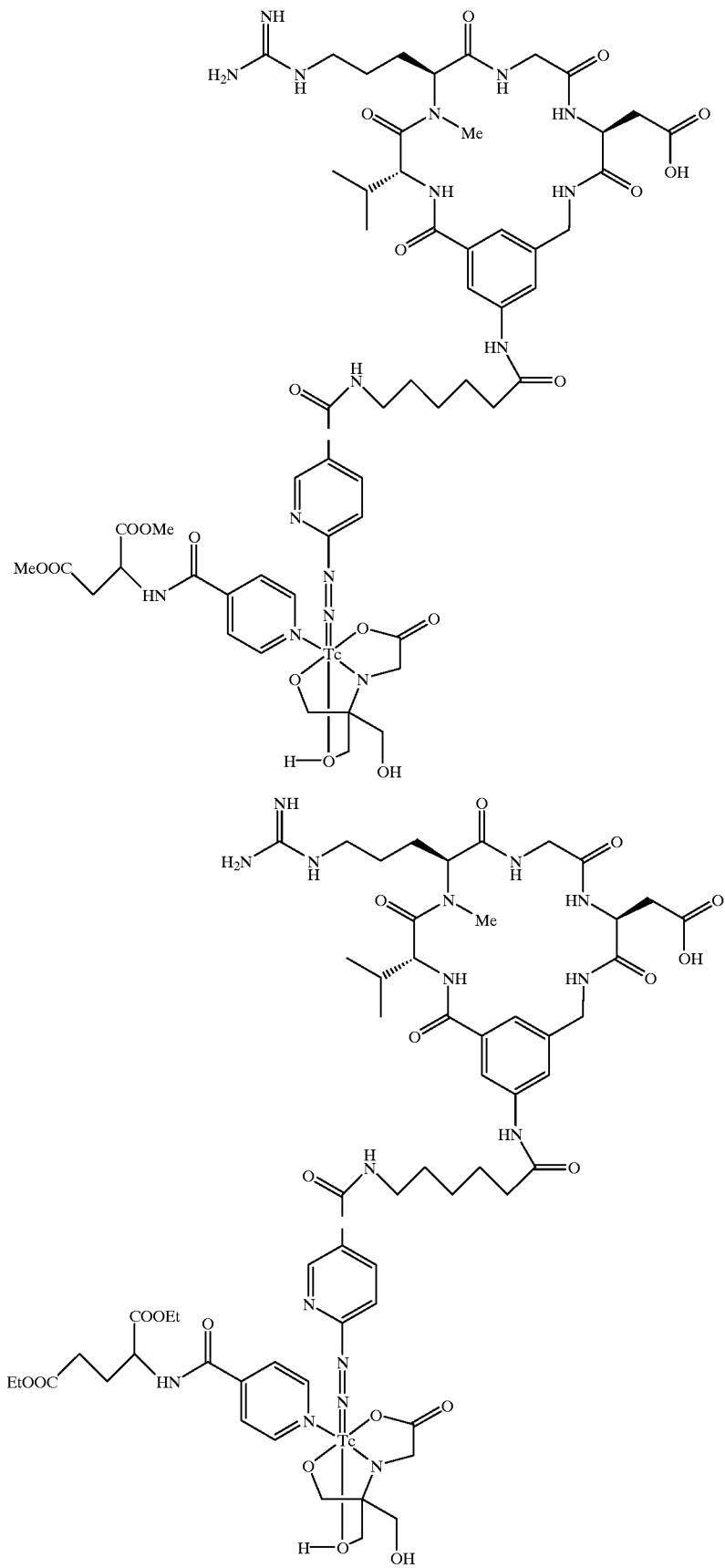

-continued
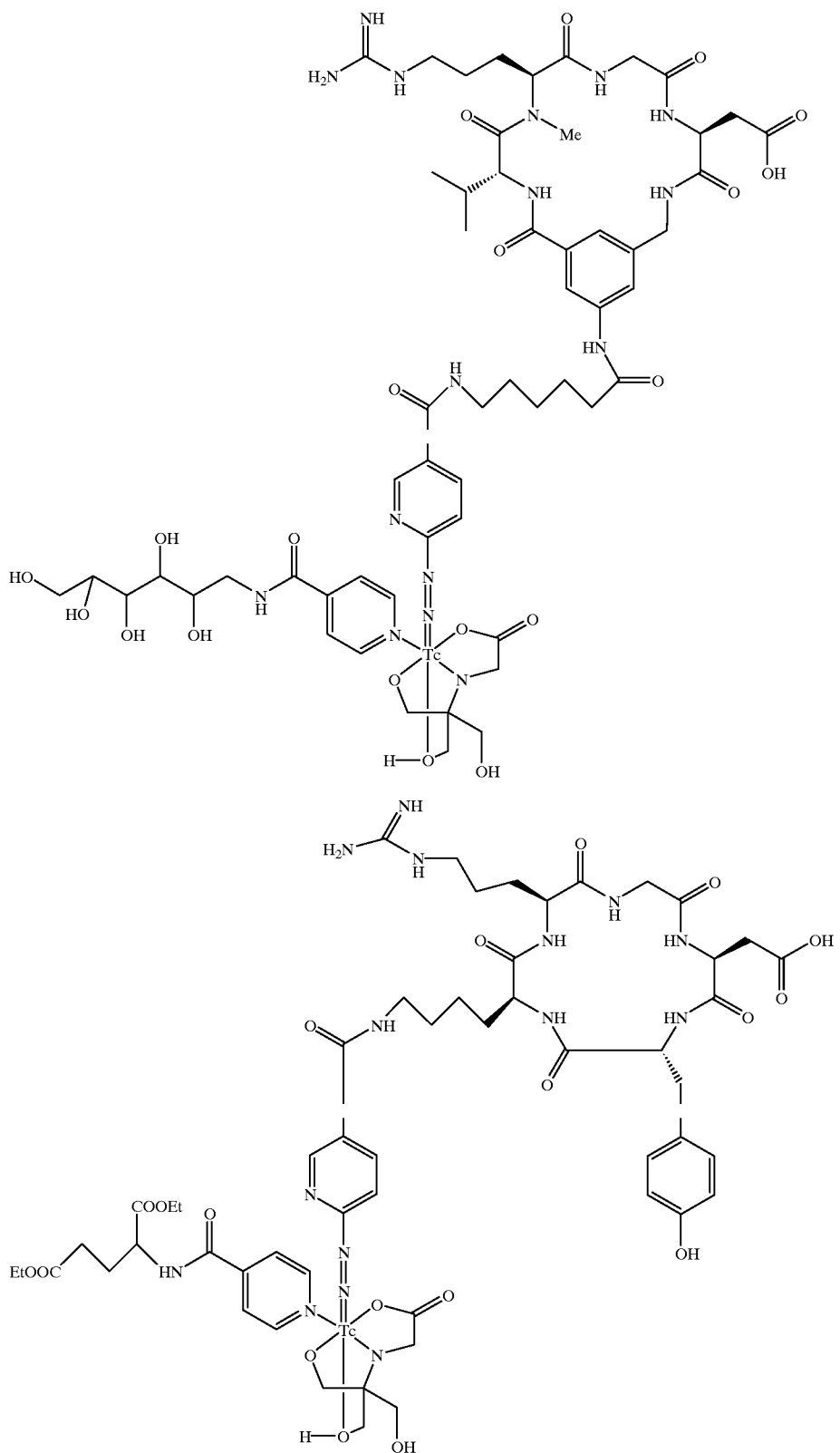

-continued
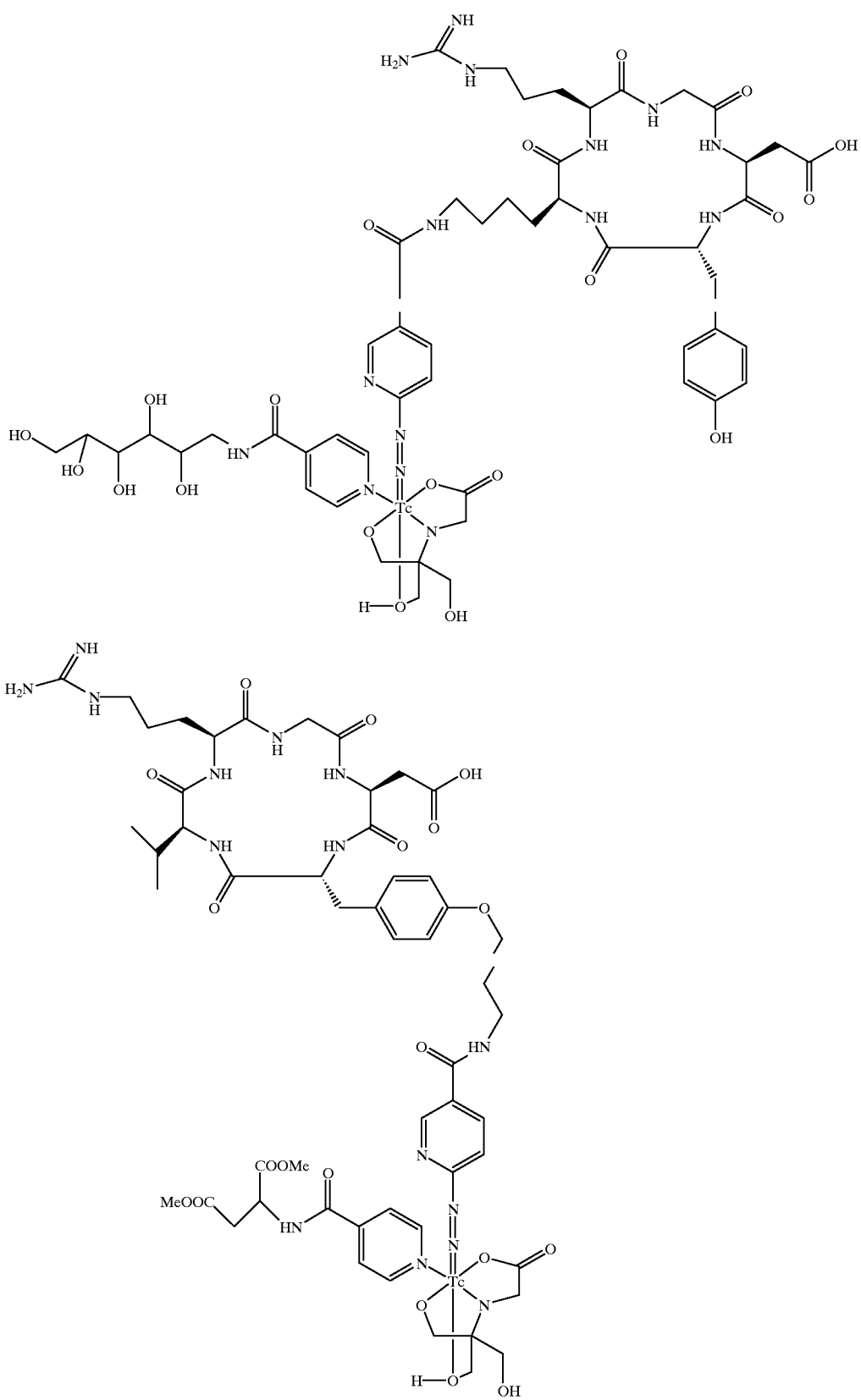

-continued
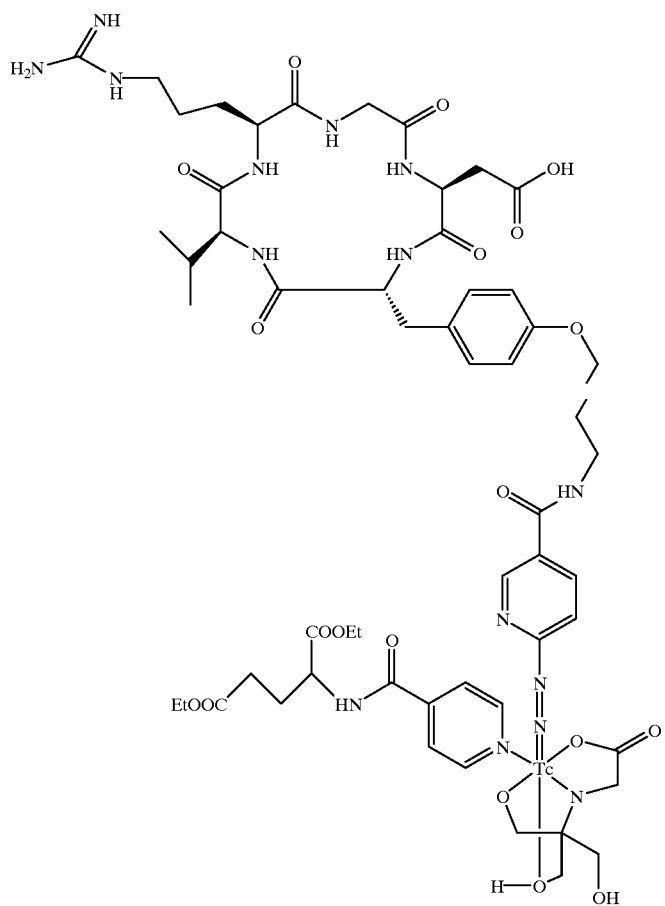
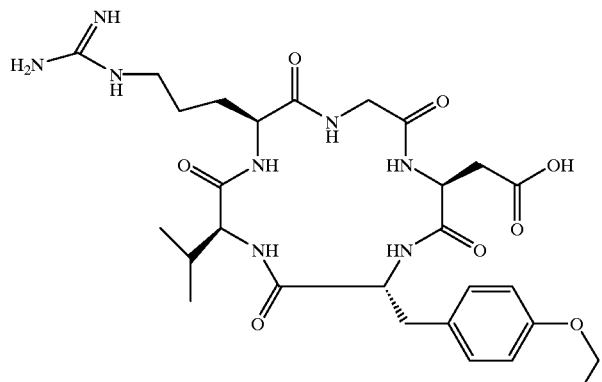

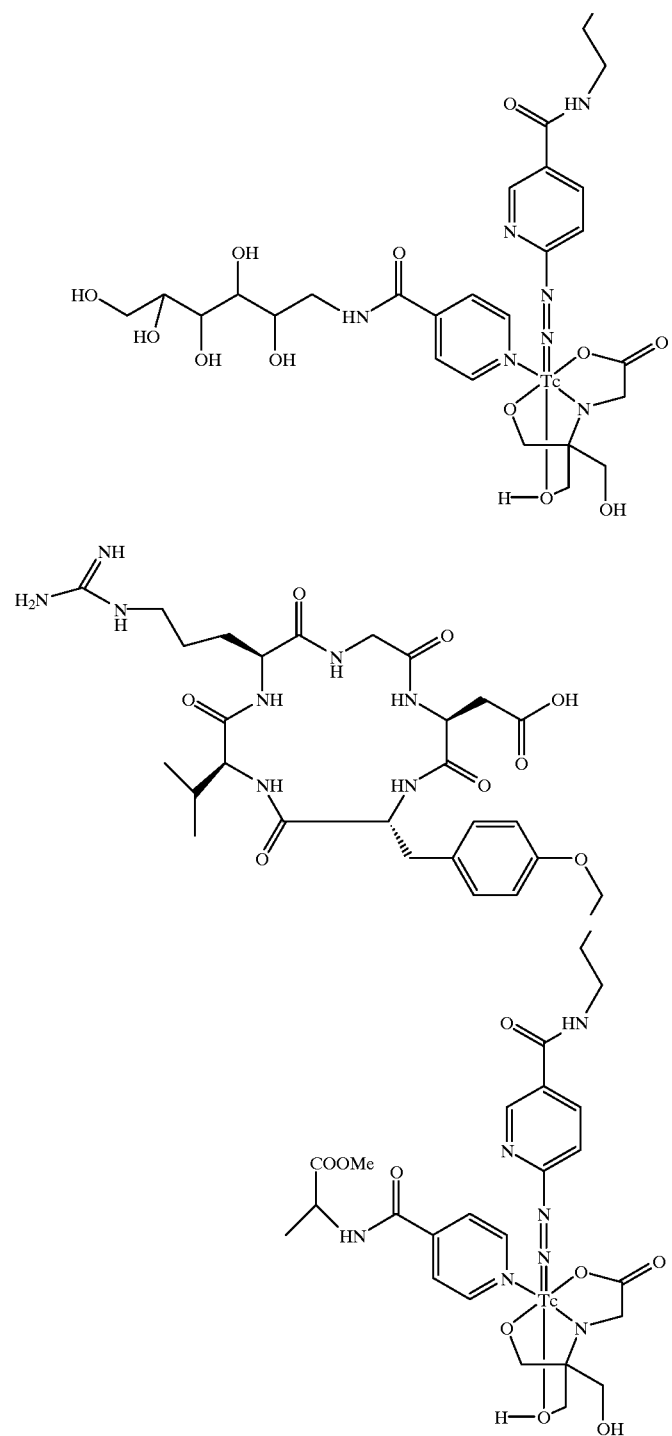

-continued
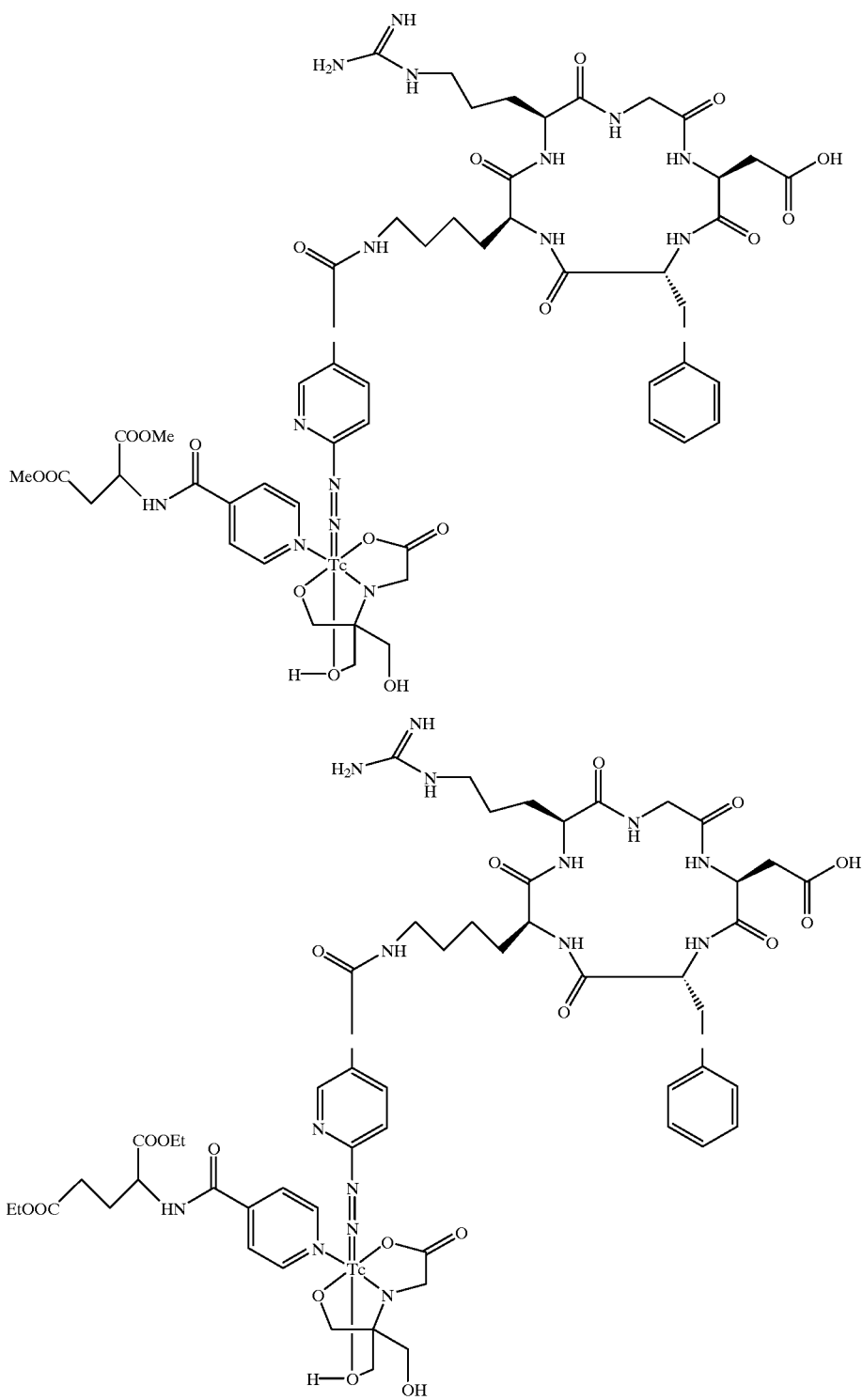

-continued

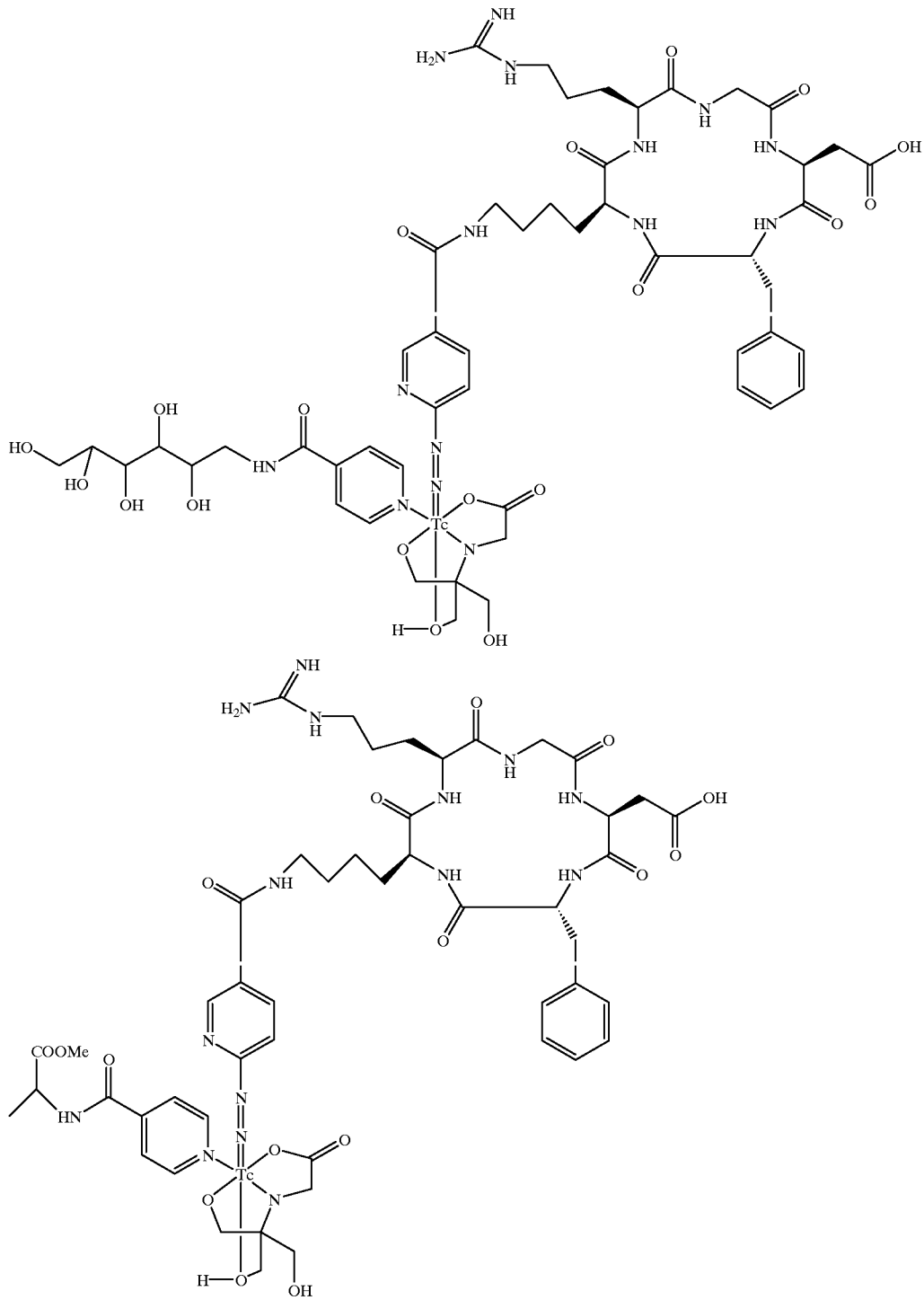

or a pharmaceutically acceptable salt form thereof.

[6] In another embodiment, the present invention provides a novel method for radioimaging a mammal comprising (i) administering to said mammal an effective amount of a radiopharmaceutical of formula (1), and (ii) scanning the mammal using a radioimaging device.

[7] In another embodiment, the present invention provides a novel method for visualizing sites of platelet deposition in a mammal by radioimaging, comprising (i) administering to said mammal an effective amount of a radiopharmaceutical of formula (1), and (ii) scanning the mammal using a radioimaging device.

[8] In another embodiment, the present invention provides a novel method of determining platelet deposition in a mammal comprising administering to said mammal a radiopharmaceutical composition of formula (1), and imaging said mammal.

[9] In another embodiment, the present invention provides a novel method of diagnosing a disorder associated with platelet deposition in a mammal comprising administering to said mammal a radiopharmaceutical composition of formula (1), and imaging said mammal.

[10] In another embodiment, the present invention provides a novel kit for preparing a radiopharmaceutical comprising:

(a) a predetermined quantity of a sterile, pharmaceutically acceptable reagent of formula:

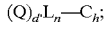

$(Q)_{d'}L_n\text{—}C_h;$ (b) a predetermined quantity of a sterile, pharmaceutically acceptable first ancillary ligand, $A_{L1}$, selected from the group: a dioxygen ligand and a functionalized aminocarboxylate;

(c) a predetermined quantity of a sterile, pharmaceutically acceptable second ancillary ligand, $A_{L2}$, of the formula:

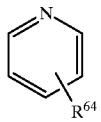

(d) a predetermined quantity of a sterile, pharmaceutically acceptable reducing agent; and (e) optionally, a predetermined quantity of one or more sterile, pharmaceutically acceptable components selected from the group: transfer ligands, buffers, lyophilization aids, stabilization aids, solubilization aids and bacteriostats;

wherein:

Q is a biologically active molecule;

d' is 1 to 20;

$L_n$ is a linking group of formula:

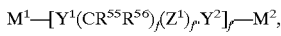

$M^1\text{—}[Y^1(CR^{55}R^{56})_f(Z^1)_{f'}Y^2]_{f''}\text{—}M^2,$ $M^1$ is $\text{—}[(CH_2)_gZ^1]_{g'}\text{—}(CR^{55}R^{56})_{g''}\text{—};$
$M^2$ is $\text{—}(CR^{55}R^{56})_{g''}\text{—}[Z^1(CH_2)_g]_{g'}\text{—};$
g is independently 0–10;
g' is independently 0–1;
g" is independently 0–10;
f is independently 0–10;
f' is independently 0–10;
f" is independently 0–1;

$Y^1$ and $Y^2$, at each occurrence, are independently selected from: a bond, O, NR56, C=O, C(=O)O, OC(=O)O, C(=O)NH—, C=NR$^{56}$, S, SO, SO$_2$, SO$_3$, NHC(=O), (NH)$_2$C(=O), and (NH)$_2$C=S;

$Z^1$ is independently selected at each occurrence from a $C_6\text{–}C_{14}$ saturated, partially saturated, or aromatic carbocyclic ring system, substituted with 0–4 R$^{57}$; and a heterocyclic ring system, optionally substituted with 0–4 R$^{57}$;

$R^{55}$ and $R^{56}$ are independently selected at each occurrence from: H, $C_1\text{–}C_{10}$ alkyl substituted with 0–5 R$^{57}$, and alkaryl wherein the aryl is substituted with 0–5 R$^{57}$;

$R^{57}$ is independently selected at each occurrence from the group: H, OH, NHR$^{58}$, C(=O)R$^{58}$, OC(=O)R$^{58}$, OC(=O)OR$^{58}$, C(=O)OR$^{58}$, C(=O)NR$^{58}$, —CN, SR$^{58}$, SOR$^{58}$, SO$_2$R$^{58}$, NHC(=O)R$^{58}$, NHC(=O)NHR$^{58}$, and NHC(=S)NHR$^{58}$, alternatively, when attached to an additional molecule Q, $R^{57}$ is independently selected at each occurrence from the group: O, NR$^{58}$, C=O, C(=O)O, OC(=O)O, C(=O)N, C=NR$^{58}$, S, SO, SO$_2$, SO$_3$, NHC(=O), (NH)$_2$C(=O), and (NH)$_2$C=S;

$R^{58}$ is independently selected at each occurrence from the group: H, $C_1\text{–}C_6$ alkyl, benzyl, and phenyl; x, y and z are independently 1 or 2;

$M_t$ is a transition metal radionuclide selected from the group: $^{99m}$Tc, $^{186}$Re and $^{188}$Re;

$C_{h'}$ is a radionuclide metal chelator coordinated to transition metal radionuclide $M_t$, and is independently selected at each occurrence, from the group: $R^{40}N=N^+=$, $R^{40}R^{41}N\text{—}N=$, and $R^{40}N=N(H)\text{—}$;

$R^{40}$ is independently selected at each occurrence from the group: a bond to $L_n$, $C_1\text{–}C_{10}$ alkyl substituted with 0–3 R$^{52}$, aryl substituted with 0–3 R$^{52}$, cycloaklyl substituted with 0–3 R$^{52}$, heterocycle substituted with 0–3 R$^{52}$, heterocycloalkyl substituted with 0–3 R$^{52}$, aralkyl substituted with 0–3 R$^{52}$ and alkaryl substituted with 0–3 R$^{52}$;

$R^{41}$ is independently selected from the group: H, aryl substituted with 0–3 R$^{52}$, $C_1\text{–}C_{10}$ alkyl substituted with 0–3 R$^{52}$, and a heterocycle substituted with 0–3 R$^{52}$;

$R^{52}$ is independently selected at each occurrence from the group: a bond to $L_n$, =O, F, Cl, Br, I, —CF$_3$, —CN, —CO$_2$R$^{53}$, —C(=O)R$^{53}$, —C(=O)N(R$^{53}$)$_2$, —CHO, —CH$_2$OR$^{53}$, —OC(=O)R$^{53}$, —OC(=O)OR$^{53a}$, —OR$^{53}$, —OC(=O)N(R$^{53}$)$_2$, —NR$^{53}$C(=O)R$^{53}$, —N(R$^{53}$)$_3$+, —NR$^{54}$C(=O)OR$^{53a}$, —NR$^{53}$C(=O)N(R$^{53}$)$_2$, —NR$^{54}$SO$_2$N(R$^{53}$)$_2$, —NR$^{54}$SO$_2$R$^{53a}$, —SO$_3$H, —SO$_2$R$^{53a}$, —SR$^{53}$, —S(=O)R$^{53a}$, —SO$_2$N(R$^{53}$)$_2$, —N(R$^{53}$)$_2$, —NHC(=NH)NHR$^{53}$, —C(=NH)NHR$^{53}$, =NOR$^{53}$, NO$_2$, —C(=O)NHOR$^{53}$, —C(=O)NHNR$^{53}$R$^{53a}$, —OCH$_2$CO$_2$H, and 2-(1-morpholino)ethoxy;

$R^{53}$, $R^{53a}$, and $R^{54}$ are each independently selected at each occurrence from the group: H, $C_1\text{–}C_6$ alkyl, and a bond to $L_n$;

$R^{64}$ is selected from the group C(O)R$^{64a}$, C(O)NR$^{67}$R$^{64a}$, and C(O)OR$^{64a}$;

$R^{64a}$ is selected from the group: $C_{1\text{-}10}$ alkyl substituted with 1–5 R$^{65}$ and 0–2 R$^{65a}$, $C_{2\text{-}10}$ alkenyl substituted with 1–5 R$^{65}$ and 0–2 R$^{65a}$, $C_{2\text{-}10}$ alkynyl substituted with 1–5 R$^{65}$ and 0–2 R$^{65a}$, aryl substituted with 1–3 R$^{65}$ and 0–2 R$^{65a}$, and $C_{3\text{-}10}$ carbocycle substituted with 1–3 R$^{65}$ and 0–2 R$^{65a}$;

$R^{65}$ is independently selected at each occurrence from the group: —OR$^{66}$, —CO$_2$R$^{66}$, —OC(=O)R$^{66}$, —OC(=O)OR$^{66}$, —OCH$_2$CO$_2$R$^{66}$, —NR$^{67}$C(=O)OR$^{66}$, —SO$_2$R$^{66a}$, —NR$^{67}$SO$_2$R$^{66a}$, and —PO$_3$R$^{66a}$;

$R^{65a}$ is independently selected at each occurrence from the group: =O, F, Cl, Br, I, —CF$_3$, —CN, —NO$_2$, —C(=O)R$^{66}$, —C(=O)N(R$^{66}$)$_2$, —N(R$^{66}$)3+, —OC(=O)N(R$^{66}$)$_2$, —NR$^{66}$C(=O)R$^{66}$, NR$^{67}$C(=O)OR$^{66a}$, —NR$^{66}$C(=O)N(R$^{66}$)$_2$, —NR$^{67}$SO$_2$N(R$^{66}$)$_2$, —SO$_2$N(R$^{66}$)$_2$, and —N(R$^{66}$)$_2$;

$R^{66}$ is independently selected at each occurrence from the group: H and $C_1\text{–}C_6$ alkyl;

$R^{66a}$ is independently selected at each occurrence from the group: H and $C_1\text{–}C_6$ alkyl; and, $R^{67}$ is independently selected at each occurrence from the group: H and $C_1\text{–}C_6$ alkyl.

In another embodiment, the present invention provides a novel radiopharmaceutical composition for use in therapy.

In another embodiment, the present invention provides the use of novel radiopharmaceutical composition for the manufacture of a medicament for imaging platelet deposition or a disorder associated with platelet deposition.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups having the specified number of carbon atoms. $C_{1-10}$ alkyl, is intended to include $C_1$, $C_2$, $C_3$, $C_4$, $C_5$, $C_6$, $C_7$, $C_8$, $C_9$, and C10 alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxyl" represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$, and $C_{10}$ alkoxy groups. Examples of alkoxy include, but are not limited to, methoxy, ethoxy, n-propoxy, i-propoxy, n-butoxy, s-butoxy, -t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl, is intended to include $C_3$, $C_4$, $C_5$, $C_6$, and $C_7$ cycloalkyl groups. Alkenyl" is intended to include hydrocarbon chains of either a straight or branched configuration and one or more unsaturated carbon-carbon bonds that may occur in any stable point along the chain, such as ethenyl and propenyl. $C_{2-10}$ alkenyl, is intended to include $C_2$, $C_3$, $C_4$, $C_5$, $C_6$, $C_7$, $C_8$, $C_9$, and $C_{10}$ alkenyl groups. "Alkynyl" is intended to include hydrocarbon chains of either a straight or branched configuration and one or more triple carbon-carbon bonds that may occur in any stable point along the chain, such as ethynyl and propynyl. $C_{2-10}$ alkynyl, is intended to include $C_2$, $C_3$, $C_4$, $C_5$, $C_6$, $C_7$, $C_8$, $C_9$, and $C_{10}$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2] bicyclooctane, fluorenyl, phenyl, naphthyl, indanyl, adamantyl, and tetrahydronaphthyl.

As used herein, the term "heterocycle" or "heterocyclic system" is intended to mean a stable 5, 6, or 7-membered monocyclic or bicyclic or 7, 8, 9, or 10-membered bicyclic heterocyclic ring that is saturated, partially unsaturated or unsaturated (aromatic), and that consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" or "heteroaryl" is intended to mean a stable 5, 6, or 7-membered monocyclic or bicyclic or 7, 8, 9, or 10-membered bicyclic heterocyclic aromatic ring that consists of carbon atoms and 1, 2, 3, or 4 heterotams independently selected from the group consisting of N, NH, O and S. It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H, 6H-1, 5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Preferred heterocycles include, but are not limited to, pyridinyl, furanyl, thienyl, pyrrolyl, pyrazolyl, pyrrolidinyl, imidazolyl, indolyl, benzimidazolyl, 1H-indazolyl, oxazolidinyl, benzotriazolyl, benzisoxazolyl, oxindolyl, benzoxazolinyl, and isatinoyl. Also included are fused ring and spiro compounds containing, for example, the above heterocycles.

The term "amino acid" as used herein means an organic compound containing both a basic amino group and an acidic carboxyl group. Included within this term are natural amino acids (e.g., L-amino acids), modified and unusual amino acids (e.g., D-amino acids), as well as amino acids which are known to occur biologically in free or combined form but usually do not occur in proteins. Included within this term are modified and unusual amino acids, such as those disclosed in, for example, Roberts and Vellaccio (1983) The Peptides, 5: 342–429, the teaching of which is hereby incorporated by reference. Natural protein occurring amino acids include, but are not limited to, alanine, arginine, asparagine, aspartic acid, cysteine, glutamic acid, glutamine, glycine, histidine, isoleucine, leucine, lysine, methionine, phenylalanine, serine, threonine, tyrosine, tryptophan, proline, and valine. Natural non-protein amino acids include, but are not limited to arginosuccinic acid, citrulline, cysteine sulfinic acid, 3,4-dihydroxyphenylalanine, homocysteine, homoserine, ornithine, 3-monoiodotyrosine, 3,5-diiodotryosine, 3,5,5,-triiodothyronine, and 3,3',5,5'-tetraiodothyronine. Modified or unusual amino acids which can be used to practice the invention include, but are not limited to, D-amino acids, hydroxylysine, 4-hydroxyproline, an N-Cbz-protected amino acid, 2,4-diaminobutyric acid, homoarginine, norleucine, N-methylaminobutyric acid, naphthylalanine, phenylglycine, β-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

The term "peptide" as used herein means a linear compound that consists of two or more amino acids (as defined herein) that are linked by means of a peptide bond. A peptide as used in the presently claimed invention is intended to refer to a moiety with a molecular weight of less than 10,000 Daltons, preferable less than 5,000 Daltons, and more preferably less than 2,500 Daltons. The term "peptide" also includes compounds containing both peptide and non-peptide components, such as pseudopeptide or peptidomimetic residues or other non-amino acid components. Such a compound containing both peptide and non-peptide components may also be referred to as a "peptide analog".

A "pseudopeptide" or "peptidomimetic" is a compound which mimics the structure of an amino acid residue or a peptide, for example, by using linking groups other than amide linkages between the peptide mimetic and an amino acid residue (pseudopeptide bonds) and/or by using non-amino acid substituents and/or a modified amino acid residue. A "pseudopeptide residue" means that portion of a pseudopeptide or peptidomimetic that is present in a peptide.

The term "peptide bond" means a covalent amide linkage formed by loss of a molecule of water between the carboxyl group of one amino acid and the amino group of a second amino acid.

The term "pseudopeptide bonds" includes peptide bond isosteres, which may be used in place of or as substitutes for the normal amide linkage. These substitute or amide "equivalent" linkages are formed from combinations of atoms not normally found in peptides or proteins which mimic the spatial requirements of the amide bond and which should stabilize the molecule to enzymatic degradation.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc . . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

The biologically active molecule Q can be a protein, antibody, antibody fragment, peptide or polypeptide, or peptidomimetic that is comprised of a recognition sequence or unit for a receptor or binding site expressed at the site of the disease, or for a receptor or binding site expressed on platelets or leukocytes. The exact chemical composition of Q is selected based on the disease state to be diagnosed, the mechanism of localization to be utilized, and to provide an optimum combination of rates of localization, clearance and radionuclidic decay.

For the purposes of this invention, the term thromboembolic disease is taken to include both venous and arterial disorders and pulmonary embolism, resulting from the formation of blood clots.

For the diagnosis of thromboembolic disorders or atherosclerosis, Q is selected from the group including the cyclic IIb/IIIa receptor antagonist compounds described in co-pending U.S. Ser. No. 08/218,861 (equivalent to WO 94/22494); the RGD containing peptides described in U.S. Pat. No. 4,578,079, U.S. Pat. No. 4,792,525, PCT US88/04403, PCT US89/01742, PCT US90/03788, PCT US91/02356 and by Ojima et. al., 204th Meeting of the Amer. Chem. Soc., 1992, Abstract 44; the peptides that are fibrinogen receptor antagonists described in European Patent Applications 90202015.5, 90202030.4, 90202032.2, 90202032.0, 90311148.2, 90311151.6, 90311537.6, the specific binding peptides and polypeptides described as IIb/IIIa receptor ligands, ligands for the polymerization site of fibrin, laminin derivatives, ligands for fibrinogen, or thrombin ligands in WO93/23085 (excluding the technetium binding groups); the oligopeptides that correspond to the IIIa protein described in WO90/00178; the hirudin-based peptides described in WO90/03391; the IIb/IIIa receptor ligands described in WO90/15818; the thrombus, platelet binding or atherosclerotic plaque binding peptides described in WO92/13572 (excluding the technetium binding group) or GB 9313965.7; the fibrin binding peptides described in U.S. Pat. No. 4,427,646 and U.S. Pat. No. 5,270,030; the hirudin-based peptides described in U.S. Pat. No. 5,279,812; or the fibrin binding proteins described in U.S. Pat. No. 5,217,705; the guanine derivatives that bind to the IIb/IIIa receptor described in U.S. Pat. No. 5,086,069; or the tyrosine derivatives described in EP 0478328A1, and by Hartman et. al., J. Med. Chem., 1992, 35, 4640; or oxidized low density lipoprotein (LDL).

For the diagnosis of infection, inflammation or transplant rejection, Q is selected from the group including the leukocyte binding peptides described in WO93/17719 (excluding the technetium binding group), WO92/13572 (excluding the technetium binding group) or U.S. Ser. No. 08/140000; the chemotactic peptides described in EP 90108734.6 or A. Fischman et. al., Semin. Nuc. Med., 1994, 24, 154; or the leukostimulatory agents described in U.S. Pat. No. 5,277,892.

For the diagnosis of cancer, Q is selected from the group of somatostatin analogs described in UK 8927255.3 or WO94/00489, the selectin binding peptides described in WO94/05269, the biological-function domains described in WO93/12819, Platelet Factor 4 or the growth factors (PDGF, EGF, FGF, TNF, MCSF or Il-8).

Q may also represent proteins, antibodies, antibody fragments, peptides, polypeptides, or peptidomimetics that bind to receptors or binding sites on other tissues, organs, enzymes or fluids. Examples include the 9-amyloid proteins that have been demonstrated to accumulate in patients with Alzheimer's disease, atrial naturetic factor derived peptides that bind to myocardial and renal receptors, antimyosin antibodies that bind to areas of infarcted tissues, or nitroimidazole derivatives that localize in hypoxic areas in vivo.

The group $C_{h'}$ is termed a hydrazido (of formula $R^{40}R^{41}N-N=$), or diazenido (of formula $R^{40}N=N^+=$ or $R^{40}N=N(H)-$) group and serves as the point of attachment of the radionuclide to the remainder of the radiopharmaceutical designated by the formula $(Q)_{d'}-L_n$ or $(Q)_{d'}$. A diazenido group can be either terminal (only one atom of the group is bound to the radionuclide) or chelating. In order to have a chelating diazenido group at least one other atom of the group, located on $R^{40}$, must also be bound to the radionuclide. The atoms bound to the metal are termed donor atoms.

The transition metal radionuclide, $M_t$, is selected from the group: technetium-99m, rhenium-186 and rhenium-188. For diagnostic purposes Tc-99m is the preferred isotope. Its 6 hour half-life and 140 keV gamma ray emission energy are almost ideal for gamma scintigraphy using equipment and procedures well established for those skilled in the art. The rhenium isotopes also have gamma ray emission energies that are compatible with gamma scintigraphy. However, they also emit high-energy beta particles that are more damaging to living tissues. These beta particle emissions can be utilized for therapeutic purposes, for example, cancer radiotherapy.

The coordination sphere of the radionuclide includes all the ligands or groups bound to the radionuclide. For a transition metal radionuclide, $M_t$, to be stable it typically has a coordination number (number of donor atoms) comprised of an integer greater than or equal to 4 and less than or equal to 8; that is there are 4 to 8 atoms bound to the metal and it is said to have a complete coordination sphere. The identity of the radionuclide, its oxidation state, and the type of donor atoms determine the requisite coordination number for a stable radionuclide complex. If the chelator or bonding unit $C_{h'}$ does not provide all of the atoms necessary to stabilize the metal radionuclide by completing its coordination sphere, the coordination sphere is completed by donor atoms from other ligands, termed ancillary or co-ligands, which can also be either terminal or chelating.

A large number of ligands can serve as ancillary or co-ligands, the choice of which is determined by a variety of considerations such as the ease of synthesis of the radiopharmaceutical, the chemical and physical properties of the ancillary ligand, the rate of formation, the yield, and the number of isomeric forms of the resulting radiopharmaceuticals, the ability to administer said ancillary or co-ligand to a patient without adverse physiological consequences to said patient, and the compatibility of the ligand in a lyophilized kit formulation. The charge and lipophilicity of the ancillary ligand will effect the charge and lipophilicity of the radiopharmaceuticals. For example, the use of 4,5-dihydroxy-1,3-benzene disulfonate results in radiopharmaceuticals with an additional two anionic groups because the sulfonate groups will be anionic under physiological conditions. The use of N-alkyl substituted 3,4-hydroxypyridinones results in radiopharmaceuticals with varying degrees of lipophilicity depending on the size of the alkyl substituents.

The radiopharmaceuticals of the present invention are comprised of two types of ancillary or co-ligands designated $A_{L1}$ and $A_{L2}$. Ancillary ligands $A_{L1}$ are comprised of two or more hard donor atoms such as oxygen and amine nitrogen ($sp^3$ hybridized). The donor atoms occupy at least two of the sites in the coordination sphere of the radionuclide metal, $M_t$; the ancillary ligand $A_{L1}$ serves as one of the three ligands in the ternary ligand system. Examples of ancillary ligands $A_{L1}$ include but are not limited to dioxygen ligands and functionalized aminocarboxylates. A large number of such ligands are available from commercial sources.

Ancillary dioxygen ligands include ligands that coordinate to the metal ion through at least two oxygen donor atoms. Examples include but are not limited to: glucoheptonate, gluconate, 2-hydroxyisobutyrate, lactate, tartrate, mannitol, glucarate, maltol, Kojic acid, 2,2-bis (hydroxymethyl) propionic acid, 4,5-dihydroxy-1,3-benzene disulfonate, or substituted or unsubstituted 1,2 or 3,4 hydroxypyridinones. (The names for the ligands in these examples refer to either the protonated or non-protonated forms of the ligands.)

Functionalized aminocarboxylates include ligands that have a combination of amine nitrogen and oxygen donor atoms. Examples include but are not limited to: iminodiacetic acid, 2,3-diaminopropionic acid, nitrilotriacetic acid, N,N'-ethylenediamine diacetic acid, N,N,N'-ethylenediamine triacetic acid, hydroxyethylethylenediamine triacetic acid, and N,N'-ethylenediamine bis-hydroxyphenylglycine. (The names for the ligands in these examples refer to either the protonated or non-protonated forms of the ligands.)

A series of functionalized aminocarboxylates are disclosed by Bridger et. al. in U.S. Pat. No. 5,350,837, herein incorporated by reference, that result in improved rates of formation of technetium labeled hydrazino modified proteins. We have determined that certain of these aminocarboxylates result in improved yields of the radiopharmaceuticals of the present invention. The preferred ancillary ligands $A_{L1}$ functionalized aminocarboxylates that are derivatives of glycine; the most preferred is tricine (tris (hydroxymethyl)methylglycine).

The second type of ancillary ligands $A_{L2}$ are highly functionalized pyridine derivatives. Ligands $A_{L2}$ are monodentate. The ancillary ligands $A_{L2}$ may be substituted with alkyl, aryl, alkoxy, heterocycle, aralkyl, alkaryl and arylalkaryl groups and may or may not bear functional groups comprised of heteroatoms such as oxygen, nitrogen, phosphorus or sulfur. Examples of such functional groups include but are not limited to hydroxyl, carboxyl, carboxamide, nitro, ether, ketone, amino, ammonium, sulfonate, sulfonamide, phosphonate, and phosphonamide. The functional groups may be chosen to alter the lipophilicity and water solubility of the ligands, which may affect the biological properties of the radiopharmaceuticals, such as altering the distribution into non-target tissues, cells or fluids, and the mechanism and rate of elimination from the body.

The radiopharmaceuticals of the present invention can be easily prepared by admixing a salt of a radionuclide, a reagent of Formula 2, an ancillary ligand $A_{L1}$, an ancillary ligand $A_{L2}$, and a reducing agent, in an aqueous solution at temperatures from room temperature to 100° C.

(2)

and pharmaceutically acceptable salts thereof, wherein: Q, d', $L_n$ are as defined above, $C_h$ is a radionuclide metal chelator selected from the group: $R^{40}R^{41}N-N=C(C_1-C_3$ alkyl$)_2$ and $R^{40}NNH_2-$, and $R^{40}R^{41}N-N=C(R^{80})(R^{81})$, and pharmaceutically acceptable salts thereof. The synthesis of reagents of formula 2 is described in WO 94/22494 and in WO 96/40637.

When $C_h$ is a hydrazone group, then it must first be converted to a hydrazine of formula $R^{40}R^{41}NNH_2$, which may or may not be protonated, prior to complexation with the metal radionuclide, $M_t$. The chelator or bonding unit, $C_{h'}$ when bound to the metal radionuclide, $M_t$, is designated $C_{h''}$. The conversion of the hydrazone group to the hydrazine can occur either prior to reaction with the radionuclide, in which case the radionuclide and the ancillary or co-ligand or ligands are combined not with the reagent but with a hydrolyzed form of the reagent bearing the chelator or bonding unit, $C_{h'}$ or in the presence of the radionuclide in which case the reagent itself is combined with the radionuclide and the ancillary or co-ligand or ligands. In the latter case, the pH of the reaction mixture must be neutral or acidic.

Alternatively, the radiopharmaceuticals of the present invention can be prepared by first admixing a salt of a radionuclide, an ancillary ligand $A_{L1}$, and a reducing agent in an aqueous solution at temperatures from room temperature to 100° C. to form an intermediate radionuclide complex with the ancillary ligand $A_{L1}$ then adding a reagent of Formula 2 and an ancillary ligand $A_{L2}$ and reacting further at temperatures from room temperature to 100° C.

Alternatively, the radiopharmaceuticals of the present invention can be prepared by first admixing a salt of a radionuclide, an ancillary ligand $A_{L1}$, a reagent of Formula 2, and a reducing agent in an aqueous solution at temperatures from room temperature to 100° C. to form an intermediate radionuclide complex, and then adding an ancillary ligand $A_{L2}$ and reacting further at temperatures from room temperature to 100° C.

The total time of preparation will vary depending on the identity of the radionuclide, the identities and amounts of the reactants and the procedure used for the preparation.

The preparations may be complete, resulting in >80% yield of the radiopharmaceutical, in 1 minute or may require more time. If higher purity radiopharmaceuticals are needed or desired, the products can be purified by any of a number of techniques well known to those skilled in the art such as liquid chromatography, solid phase extraction, solvent extraction, dialysis or ultrafiltration.

The technetium and rhenium radionuclides are preferably in the chemical form of pertechnetate or perrhenate and a pharmaceutically acceptable cation. The pertechnetate salt form is preferably sodium pertechnetate such as obtained from commercial Tc-99m generators. The amount of pertechnetate used to prepare the radiopharmaceuticals of the present invention can range from 0.1 mCi to 1 Ci or more preferably from 1 to 200 mCi.

The amount of the reagent of formula 2 used to prepare the radiopharmaceuticals of the present invention can range from 0.1 μg to 10 mg, or more preferably from 0.5 μg to 100 μg. The amounts of the other reactants and the identity of the radiopharmaceuticals of Formula 1 to be prepared will dictate the amount used.

The amounts of the ancillary ligands $A_{L1}$ used can range from 0.1 mg to 1 g or more preferably from 1 mg to 100 mg. The exact amount for a particular radiopharmaceutical is a function of identity of the radiopharmaceuticals of Formula 1 to be prepared, the procedure used and the amounts and identities of the other reactants. Too large an amount of $A_{L1}$ will result in the formation of by-products comprised of technetium labeled $A_{L1}$ without a biologically active molecule or by-products comprised of technetium labeled biologically active molecules with the ancillary ligand $A_{L1}$ but without the ancillary ligand $A_{L2}$. Too small an amount of $A_{L1}$ will result in other by-products such as technetium labeled biologically active molecules with the ancillary ligand $A_{L2}$ but without the ancillary ligand $A_{L1}$, or reduced hydrolyzed technetium, or technetium colloid. The amounts of the ancillary ligands $A_{L2}$ used can range from 0.001 mg to 1 g or more preferably from 0.01 mg to 10 mg. The exact amount for a particular radiopharmaceutical is a function of the identity of the radiopharmaceuticals of Formula 1 to be prepared, the procedure used and the amounts and identities of the other reactants. Too large an amount of $A_{L2}$ will result in the formation of by-products comprised of technetium labeled $A_{L2}$ without a biologically active molecule or by-products comprised of technetium labeled biologically active molecules with the ancillary ligand $A_{L2}$ but without the ancillary ligand $A_{L1}$. If the moiety $(Q)_{d'}$—$L_n$—$C_h$ bears one or more substituents that are comprised of a soft donor atom, as defined above, at least a ten-fold molar excess of the ancillary ligand $A_{L2}$ to the reagent of formula 2 is required to prevent the substituent from interfering with the coordination of the ancillary ligand $A_{L2}$ to the metal radionuclide, $M_t$.

Suitable reducing agents for the synthesis of the radiopharmaceuticals of the present invention include stannous salts, dithionite or bisulfite salts, borohydride salts, and formamidinesulfinic acid, wherein the salts are of any pharmaceutically acceptable form. The preferred reducing agent is a stannous salt. The amount of a reducing agent used can range from 0.001 mg to 10 mg or more preferably from 0.005 mg to 1 mg. The specific structure of a radiopharmaceutical of the present invention will depend on the identity of the biologically active molecule Q, the number d', the identity of the linker $L_n$, the identity of the chelator moiety $C_h$, the identity of the ancillary ligand $A_{L1}$, the identity of the ancillary ligand $A_{L2}$, and the identity of the radionuclide $M_t$. The identities of Q, $L_n$, and $C_{h'}$ and the number d' are determined by the choice of the reagent of Formulae 2 or 3. For a given reagent of Formulae 2 or 3, the amount of the reagent, the amount and identity of the ancillary ligands $A_{L1}$ and $A_{L2}$, the identity of the radionuclide $M_t$ and the synthesis conditions employed will determine the structure of the radiopharmaceutical of Formula 1.

Radiopharmaceuticals synthesized using concentrations of reagents of Formulae 2 or 3 of <100 μg/mL, will be comprised of one hydrazido or diazenido group $C_h$; the value of x will be 1. Those synthesized using >1 mg/mL concentrations will be comprised of two hydrazido or diazenido groups; the value of x will be 2. The two $C_h$ groups may be the same or different. For most applications, only a limited amount of the biologically active molecule can be injected and not result in undesired side effects, such as chemical toxicity, interference with a biological process or an altered biodistribution of the radiopharmaceutical. Therefore, the radiopharmaceuticals with x equal to 2, which require higher concentrations of the reagents of Formula 2 comprised in part of the biologically active molecule, will have to be diluted or purified after synthesis to avoid such side-effects.

The identities and amounts used of the ancillary ligands $A_{L1}$ and $A_{L2}$ will determine the values of the variables y and z. The values of y and z can independently be an integer from 1 to 2. In combination, the values of y and z will result in a technetium coordination sphere that is made up of at least five and no more than seven donor atoms. For monodentate ancillary ligands $A_{L2}$, z can be an integer from 1 to 2; for bidentate or tridentate ancillary ligands $A_{L2}$, z is 1. The preferred combination for monodentate ligands is y equal to 1 or 2 and z equal to 1. The preferred combination for bidentate or tridentate ligands is y equal to 1 and z equal to 1.

Another aspect of the present invention are diagnostic kits for the preparation of radiopharmaceuticals useful as imaging agents for the diagnosis of cardiovascular disorders, infectious disease, inflammatory disease and cancer. Diagnostic kits of the present invention comprise one or more vials containing the sterile, non-pyrogenic, formulation comprised of a predetermined amount of the reagent of formulae $(Q)_{d'}$—$L_n$—$C_h$ or $(Q)_{d'}$—$L_n$—$H_2$, one or two ancillary or co-ligands and optionally other components such as reducing agents, transfer ligands, buffers, lyophilization aids, stabilization aids, solubilization aids and bacteriostats. The inclusion of one or more optional components in the formulation will frequently improve the ease of synthesis of the radiopharmaceutical by the practicing end user, the ease of manufacturing the kit, the shelf-life of the kit, or the stability and shelf-life of the radiopharmaceutical. The improvement achieved by the inclusion of an optional component in the formulation must be weighed against the added complexity of the formulation and added cost to manufacture the kit. The one or more vials that contain all or part of the formulation can independently be in the form of a sterile solution or a lyophilized solid.

Buffers useful in the preparation of radiopharmaceuticals and in diagnostic kits useful for the preparation of said radiopharmaceuticals include but are not limited to phosphate, citrate, sulfosalicylate, and acetate. A more complete list can be found in the *United States PharmacoDeia*.

Lyophilization aids useful in the preparation of diagnostic kits useful for the preparation of radiopharmaceuticals include but are not limited to mannitol, lactose, sorbitol, dextran, Ficoll, and polyvinylpyrrolidine (PVP).

Stabilization aids useful in the preparation of radiopharmaceuticals and in diagnostic kits useful for the preparation of said radiopharmaceuticals include but are not limited to ascorbic acid, cysteine, monothioglycerol, sodium bisulfite, sodium metabisulfite, gentisic acid, and inositol.

Solubilization aids useful in the preparation of radiopharmaceuticals and in diagnostic kits useful for the preparation of said radiopharmaceuticals include but are not limited to ethanol, glycerin, polyethylene glycol, propylene glycol, polyoxyethylene sorbitan monooleate, sorbitan monooloeate, polysorbates, poly(oxyethylene)poly(oxypropylene)poly(oxyethylene) block copolymers (Pluronics) and lecithin. Preferred solubilizing aids are polyethylene glycol, and Pluronics.

Bacteriostats useful in the preparation of radiopharmaceuticals and in diagnostic kits useful for the preparation of said radiopharmaceuticals include but are not limited to benzyl alcohol, benzalkonium chloride, chlorbutanol, and methyl, propyl or butyl paraben.

A component in a diagnostic kit can also serve more than one function. A reducing agent can also serve as a stabilization aid, a buffer can also serve as a transfer ligand, a lyophilization aid can also serve as a transfer, ancillary or co-ligand and so forth.

The predetermined amounts of each component in the formulation are determined by a variety of considerations that are in some cases specific for that component and in other cases dependent on the amount of another component or the presence and amount of an optional component. In general, the minimal amount of each component is used that will give the desired effect of the formulation. The desired effect of the formulation is that the practicing end user can synthesize the radiopharmaceutical and have a high degree of certainty that the radiopharmaceutical can be safely injected into a patient and will provide diagnostic information about the disease state of that patient.

The diagnostic kits of the present invention will also contain written instructions for the practicing end user to follow to synthesize the radiopharmaceuticals. These instructions may be affixed to one or more of the vials or to the container in which the vial or vials are packaged for shipping or may be a separate insert, termed the package insert.

Another aspect of the present invention contemplates a method of imaging the site of thrombotic disease in a patient involving: (1) synthesizing a radiopharmaceutical using a reagent of the present invention capable of localizing at sites of thrombotic disease due to an interaction between the biologically active group, Q, of the radiopharmaceutical and a receptor or binding site expressed at the site of the disease or with a receptor or binding site on an endogenous blood component that accumulates at the site; (2) administering said radiopharmaceutical to a patient by injection or infusion; (3) imaging the patient using either planar or SPECT gamma scintigraphy.

Another aspect of the present invention contemplates a method of imaging the site of infection or infectious disease in a patient involving: (1) synthesizing a radiopharmaceutical using a reagent of the present invention capable of localizing at sites of infection or infectious disease due to an interaction between the biologically active group, Q, of the radiopharmaceutical and a receptor or binding site expressed at the site of the disease or with a receptor or binding site on an endogenous blood component that accumulates at the site; (2) administering said radiopharmaceutical to a patient by injection or infusion; (3) imaging the patient using either planar or SPECT gamma scintigraphy.

Another aspect of the present invention contemplates a method of imaging the site of inflammation in a patient involving: (1) synthesizing a radiopharmaceutical using a reagent of the present invention capable of localizing at sites of inflammation due to an interaction between the biologically active group, Q, of the radiopharmaceutical and a receptor or binding site expressed at the site of inflammation or with a receptor or binding site on an endogenous blood component that accumulates at the site; (2) administering said radiopharmaceutical to a patient by injection or infusion; (3) imaging the patient using either planar or SPECT gamma scintigraphy.

Another aspect of the present invention contemplates a method of imaging the site of cancer in a patient involving: (1) synthesizing a radiopharmaceutical using a reagent of the present invention capable of localizing at sites of cancer due to an interaction between the biologically active group, Q, of the radiopharmaceutical and a receptor or binding site expressed at the site of the cancer or with a receptor or binding site on an endogenous blood component that accumulates at the site; (2) administering said radiopharmaceutical to a patient by injection or infusion; (3) imaging the patient using either planar or SPECT gamma scintigraphy.

The radiopharmaceuticals are administered by intravenous injection, usually in saline solution, at a dose of 1 to 100 mCi per 70 kg body weight, or preferably at a dose of 5 to 50 mCi. Imaging is performed using known procedures.

Other features of the invention will become apparent in the course of the following descriptions of exemplary embodiments which are given for illustration of the invention and are not intended to be limiting thereof.

EXAMPLES

1-Amino-1-deoxy-D-sorbitol, L-aspartic acid dimethyl ester hydrochloride, L-glutamic acid diethyl ester hydrochloride, isonicotinoyl chloride hydrochloride, and N-(2-hydroxyethyl)isonicotinamide, were purchased from Aldrich. $Na^{99m}TcO_4$ was obtained from a Technelite® $^{99}Mo/^{99m}Tc$ generator, DuPont Pharma, North Billerica, Mass.

Instruments.

$^1$H NMR spectra were recorded on a 270 MHz Bruker spectrometer. The $^1$H NMR data were reported as δ (ppm) relative to TMS. Electrospray MS analyses were performed using a VG Quattro mass spectrometer. LC-MS spectra were collected using a HP1100 LC/MSD system with API-electrospray interface. The high-performance liquid HPLC methods used a Hewlett Packard Model 1090 instrument with radiometric detector using a sodium iodide probe.

Synthesis of Coligands.

Functionalized pyridine analogs were synthesized by reacting isonicotinyl chloride hydrochloride with the corresponding amino acid diester in chloroform in the presence of excess triethylamine. In case of 1-amino-1-deoxy-D-sorbitol, DMF was used as the solvent due to the poor solubility of 1-amino-1-deoxy-D-sorbitol in chloroform or acetonitrile. The functionalized pyridine analogs were isolated and characterized by $^1$H NMR and electrospray mass spectroscopy.

Preparation of ISONIC-Asp-OMe2 (L1)

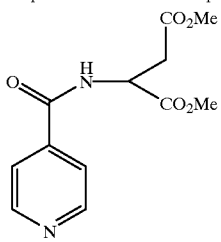

To a solution of L-aspartic acid dimethyl ester hydrochloride (2.0 g, 10 mmol) in chloroform (100 mL) was added isonicotinoyl chloride hydrochloride (1.8 g, 10 mmol) and triethylamine (3.0 mL, 21.5 mmol). The reaction mixture was refluxed for 2 h, and then stirred at room temperature for 24 h. The solution was filtered and the filtrate was evaporated to give a whitish oil. This residue was dissolved in 20 mL $H_2O$, and was then extracted with ethyl acetate (2×100 mL). The organic phases were combined, washed with $H_2O$ (50 mL), and dried over $Na_2SO_4$. Removal of ethyl acetate gave a whitish oil, isonicotinoyl aspartic acid dimethyl ester. Electrospray MS: m/z=267 (M+1, $[C_{12}H_{14}N_2O_5]^+$) $^1H$ NMR ($CDCl_3$): 2.91–3.17 (m, 2H, $CH_2$), 3.69 (s, 3H, $COOCH_3$), 3.78 (s, 3H, $COOCH_3$), 4.99–5.05 (m, 1H, CH), 7.38–7.41 (d, 1H, NH), 7.62–7.65 (m, 2H, py), 7.82–7.84 (m, 2H, py).

Preparation of ISONIC-Glu-OEt2 (L2)

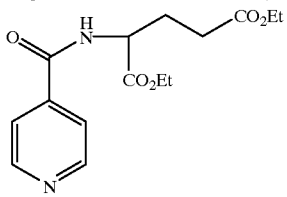

The title compound was prepare using the same procedure as described for ISONIC-Asp-OMe2. It was isolated as a crystalline solid. Electrospray MS: m/z=309 (M+1, $[C_{15}H_{20}N_2O_5]^+$). $^1H$ NMR ($CDCl_3$): 1.16–1.28 (m, 6H, $CH_3$), 1.9–2.7 (m, 4H, $CH_2CH_2$), 3.9–4.3 (m, 4H, $COOCH_2$), 4.6–4.8 (m, 1H, CH), 7.64–7.66 (m, 2H, py), 7.80–7.82 (d, 1H, NH), 8.69–8.71 (m, 2H, py).

Preparation of ISONIC-Ala-OMe (L3)

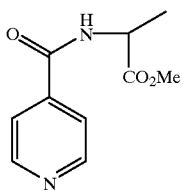

To a chilled solution of L-alanine methyl ester hydrochloride (1.4 g, 10 mmol) in chloroform (100 mL) was added isonicotinoyl chloride hydrochloride (1.8 g, 10 mmol) and triethylamine (4.5 mL, 32.2 mmol). The reaction mixture was heated to reflux for 2 h then stirred at room temperature for 18 h. The solution was evaporated under reduced pressure to give a white solid. This residue was washed with diethyl ether (2×100 mL). It was then filtered and the filtrate was evaporated to give the expected product as a yellow oil. Electrospray MS: m/z=209 (M+1, $[C_{10}H_{12}N_2O_3]^+$). $^1H$ NMR ($CDCl_3$): 1.47–1.50 (d, 3H, $CH_3$), 3.75 (s, 3H, $COOCH_3$), 4.72–4.78 (m, 1H, CH), 7.05–7.21 (d, 1H, NH), 7.59–7.61 (m, 2H, py), 8.67–8.69 (m, 2H, y).

Preparation of ISONIC-Sorb (L4)

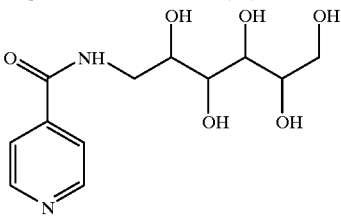

To a solution of 1-aminodeoxy-D-sorbitol (1.8 g, 10 mmol) in DMF (100 mL) in a bath of dry ice and isopropyl alcohol was added isonicotinoyl chloride hydrochloride (1.8 g, 10 mmol) and triethylamine (3.0 mL, 21.5 mmol). The reaction mixture was slowly brought to room temperature then stirred at RT for 48 h. The solution was filtered and the filtrate was evaporated under reduced pressure to give a tan-colored solid, which was then washed with methanol and dried under vaccuum for 3 h to provide the title compound.

The yield was 2.5 g. Electrospray MS: m/z=287 (M+1, $[C_{12}H_{18}N_2O_6]^+$). $^1H$ NMR ($D_2O$): 3.49–4.09 (m, 8H, CH, $CH_2$), 7.73–7.75 (m, 2H, py), 8.67–8.73 (m, 2H, py).

A General Procedure for the $^{99m}Tc$-Labeling of HYNIC-Modified Biomolecules.

To a sealed 10 mL vial was added 0.4 mL of tricine solution (50–100 mg/mL in 25 mM succinate buffer, pH=5.0), 0.2 mL of HYNIC-BM solution (100 μg/mL in 25 mM succinate buffer or a 50:50 mixture of ethanol and 25 mM succinate buffer, pH=5.0), 0.2 mL of coligand solution (50 mg/mL in 50% aqueous ethanol), 0.2 mL of $^{99m}TcO_4^-$ solution (200 mCi/mL in saline), and 25 μL of $SnCl_2.2H_2O$ solution (1.0 mg/mL in 0.1 N HCl). The vial was heated at 100° C. for 20 min. After cooling at room temperature, the reaction mixture was analyzed by radio-HPLC and ITLC.

The TLC method used Gelman Sciences silica-gel paper strips and a 1:1 mixture of acetone and saline as eluant. The HPLC Method used a Zorbax C18, 250×4.6 mm Column and a flow rate of 1.0 mL/min. The mobile Phase A contains 10 mM sodium phosphate buffer (pH=6.0) and the mobile phase B is 100% acetonitrile. The following gradients were used for the characterization of [$^{99m}Tc$]HYNICtide complexes.

| Gradient A | | | | | | |
|---|---|---|---|---|---|---|
| t (min) | 0 | 30 | 31 | 36 | 37 | 45 |
| % B | 12 | 40 | 75 | 75 | 12 | 12 |
| Gradient B | | | | | | |
| t (min) | 0 | 20 | 21 | 26 | 37 | 35 |
| % B | 0 | 25 | 75 | 75 | 0 | 0 |
| Gradient C | | | | | | |
| t (min) | 0 | 20 | 30 | 31 | 40 | |
| % B | 0 | 20 | 75 | 0 | 0 | |

-continued

| Gradient D | | | | | |
|---|---|---|---|---|---|
| t (min) | 0 | 20 | 30 | 31 | 40 |
| % B | 0 | 75 | 75 | 0 | 0 |

Ternary Ligand [$^{99m}$Tc]HYNIC-BM Complexes.

New [$^{99m}$Tc]HYNIC-BM complexes were prepared by direct reduction of [$^{99m}$Tc]pertechnetate with stannous chloride in the presence of HYNIC-BM, tricine and a pyridine coligand. The yields for ternary ligand complexes [$^{99m}$Tc(HYNICtide)(tricine)(L)] (L=functionalized pyridine analogs) were >70%. Tricine concentration can range from 20 to 60 mg/mL. Using lower tricine concentrations (<20 mg/mL) may result in the formation of a significant amount of [$^{99m}$Tc]colloid. The pyridine coligand concentration was 5–10 mg/mL. The concentration of the HYNIC-BM can range from 10 to 50 µg/mL for 50 mCi of [$^{99m}$Tc] pertechnetate.

Table I summarizes the radio-HPLC data for ternary ligand [$^{99m}$Tc]HYNIC-BM complexes. In most cases, the ternary ligand complex shows two radiometric peaks in the HPLC chromatogram due to the resolution of two diastereomers of the [$^{99m}$Tc]HYNIC-BM complexes. (Separation of the two isomeric forms for the complex [$^{99m}$Tc(HYNICtide)(tricine)(L)] (L=ISONIC-SORB) was very difficult due to high hydrophilicity.)

Example 1

[$^{99m}$Tc(a)(tricine)(Isonic-Asp-OMe2)]

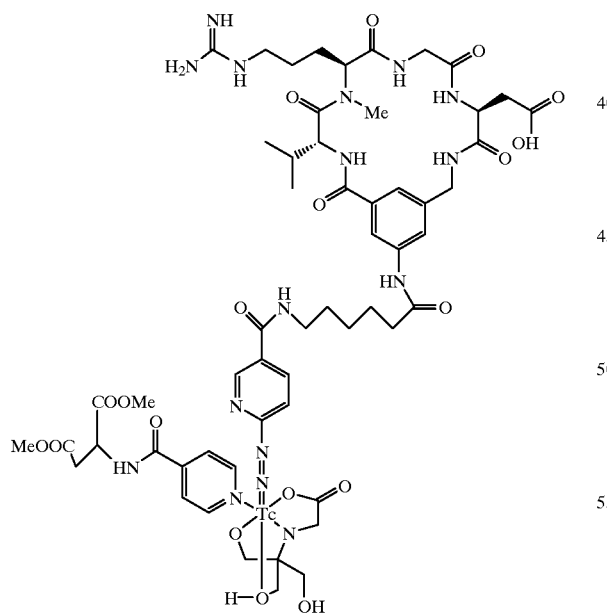

Example 2

[$^{99m}$Tc(a)(tricine)(Isonic-Glu-OEt$_2$)]

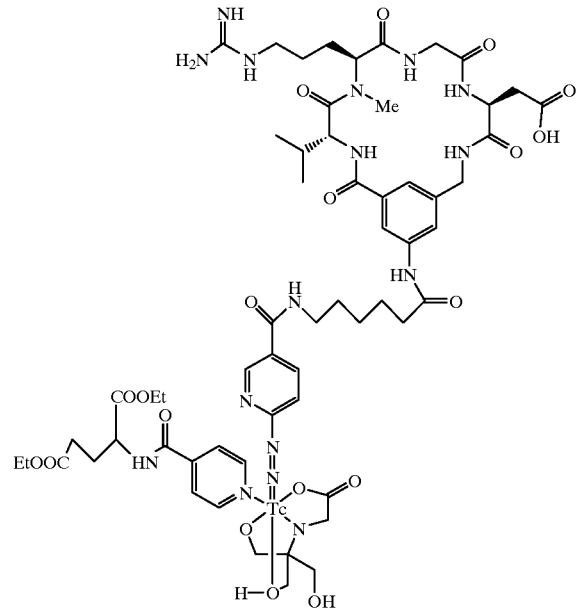

Example 3

[$^{99m}$Tc(a)(tricine)(Isonic-Sorb)]

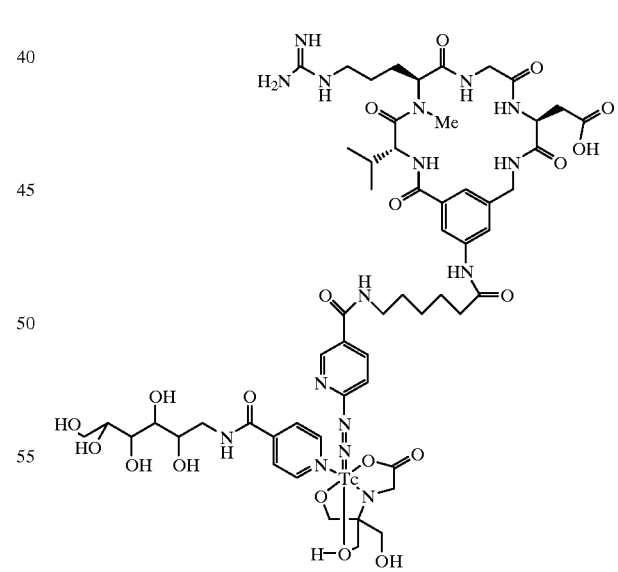

Example 4
[$^{99m}$Tc(b)(tricine)(Isonic-Glu-OEt$_2$)]
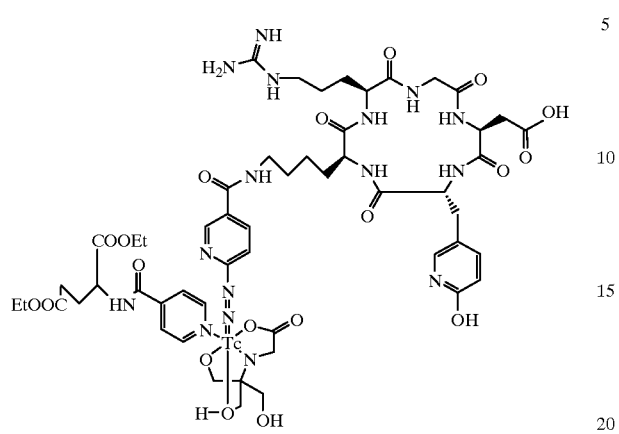
Example 5
[$^{99m}$Tc(b)(tricine)(Isonic-Sorb)]
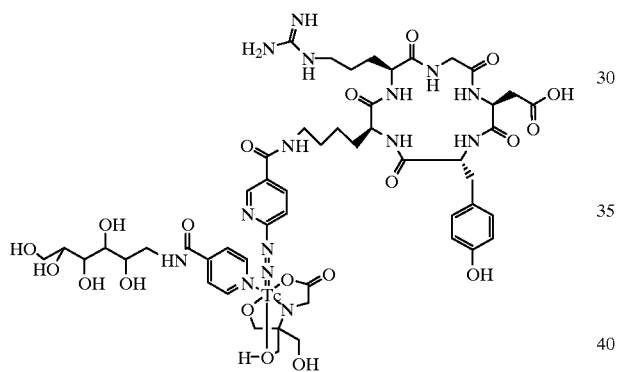
Example 6
[$^{99m}$Tc(c)(tricine)(Isonic-Asp-OMe$_2$)]
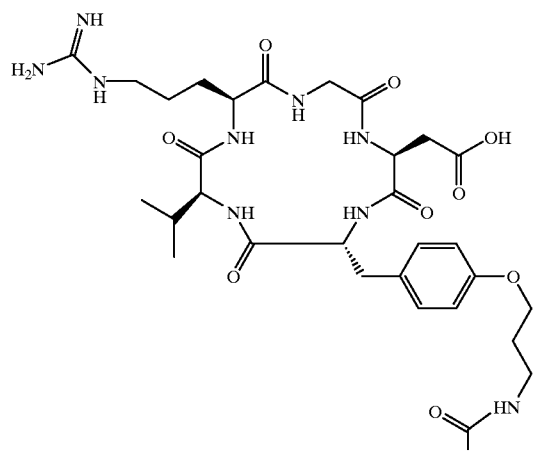
-continued
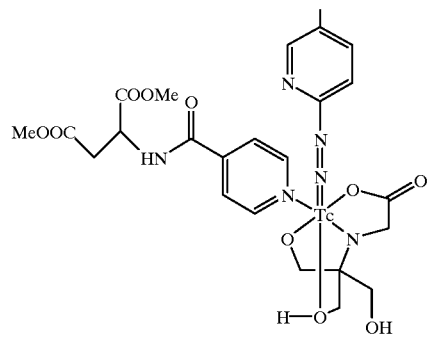
Example 7
[n$^{99}$Tc(c)(tricine)(Isonic-Glu-OEt$_2$)]
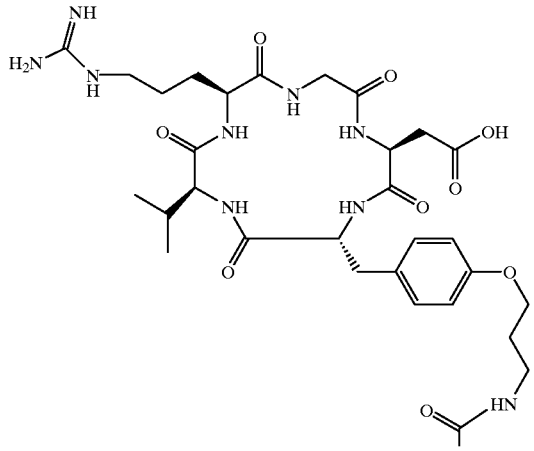
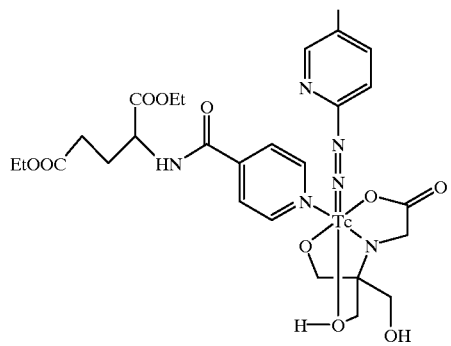

Example 8
[$^{99m}$Tc(c)(tricine)(Isonic-Sorb)]
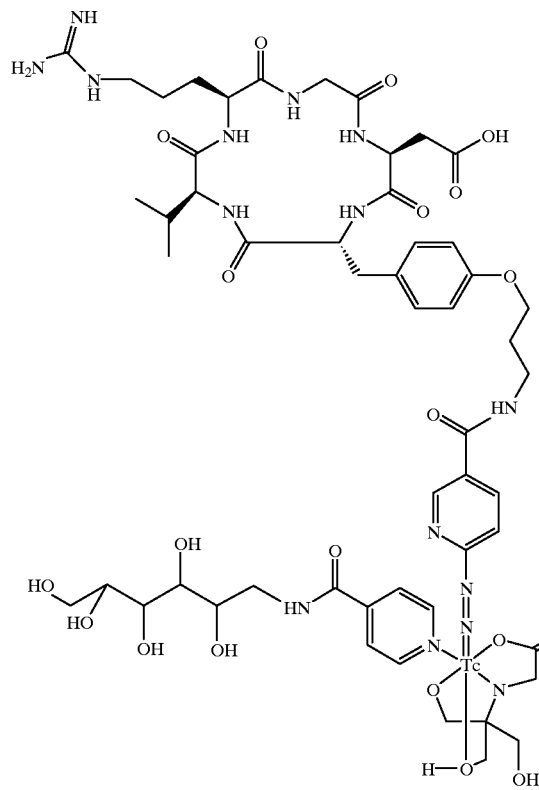
Example 9
[$^{99m}$Tc(c)(tricine)(Isonic-Ala-OMe)]
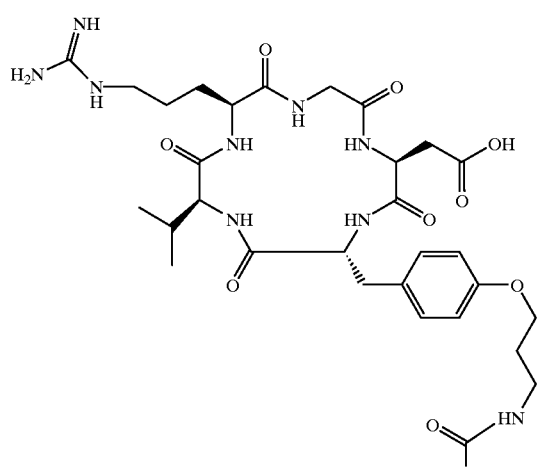
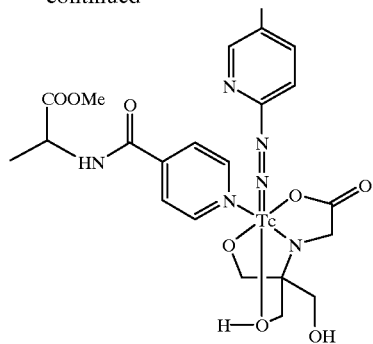
Example 10
[$^{99m}$Tc(d)(tricine)(Isonic-Asp-OMe$_2$)]
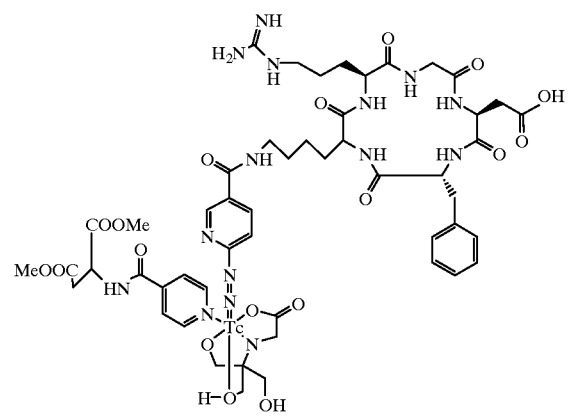
Example 11
[$^{99m}$Tc(d)(tricine)(Isonic-Glu-OEt$_2$)]
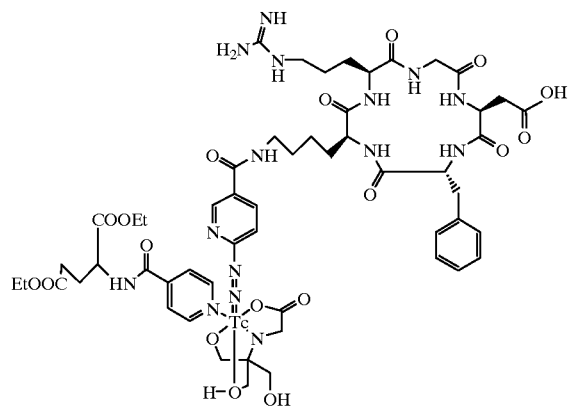

Example 12
[$^{99m}$Tc(d)(tricine)(Isonic-Sorb)]

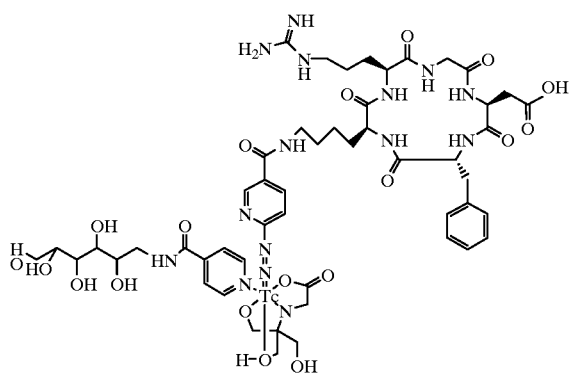

Example 13
[$^{99m}$Tc(d)(tricine)(Isonic-Ala-OMe)]

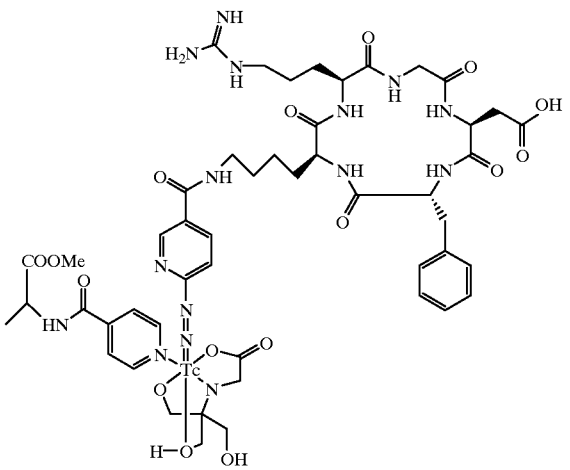

HYNIC-BM a—cyclo(D-Val-NMeArg-Gly-Asp-Mamb(5-(6-(HYNIC)hexanamide))))
b—cyclo(Arg-Gly-Asp-D-Tyr-ω-(HYNIC)-Lys)
c—cyclo(Arg-Gly-Asp-D-(O-(3-(HYNIC)amidopropyl)-Tyr-•-(HYNIC)-Val)
d—cyclo(Arg-Gly-Asp-D-Phe-ω-(HYNIC)-Lys)

TABLE 1

New ternary ligand complexes, [Tc(ISONIC-BM)(tricine)(Ligand)], and their HPLC data.

| Ex. # | ISONIC-R | HYNIC-BM | Ligand Type | Gradient | RT's (min) | % RCP |
|---|---|---|---|---|---|---|
| 1 | ISONIC-Asp(OMe)$_2$ | a | IIb/IIIa | A | 13.7 / 15.3 | 95.3 |
| 2 | ISONIC-Glu(OEt)$_2$ | a | IIb/IIIa | B | 11.1 / 11.9 | 87.7 |
| 3 | ISONIC-Sorb | a | IIb/IIIa | B | 9.0 | 100.0 |
| 4 | ISONIC-Glu(OEt)$_2$ | b | VRA | B | 9.7 / 11.1 | 91.3 |
| 5 | ISONIC-Sorb | b | VRA | B | 7.3 | 92.1 |
| 6 | ISONIC-ASP(OMe)$_2$ | c | VRA | C | 24.9 / 25.4 | 96.5 |
| 7 | ISONIC-Glu(OMe)$_2$ | c | VRA | C | 25.4 / 26.0 | 94.2 |
| 8 | ISONIC-Sorb | c | VRA | C | 18.8 | 89.8 |
| 9 | ISONIC-Ala(OMe) | c | VRA | C | 23.9 | 94.7 |
| 10 | ISONIC-Asp(OMe)$_2$ | d | VRA | C | 23.3 / 24.4 | 89.7 |
| 11 | ISONIC-Glu(OMe)$_2$ | d | VRA | C | 24.5 / 25.2 | 97.3 |
| 12 | ISONIC-Sorb | d | VRA | C | 16.4 | 88.1 |
| 13 | ISONIC-Ala(OMe) | d | VRA | C | 22.4 | 88.4 |

VRA = vitronectin receptor antagonists

Complexes, [$^{99m}$Tc(HYNICtide) (tricine) (L)] (L=ISONIC-AspOMe$_2$ and ISONIC-Sorb), were analyzed using LC-MS at the tracer level. The LC-MS results are summarized in Table 2. Both complexes were detected in their acid form, and showed the expected monocationic molecular ions, $(M+1)^+$ and a predominant peak for the dicationic molecular ions, $(M+2)^{2+}$. Both monocationic and dicationic molecular ions are useful for identification of these complexes.

TABLE 2

LC-MS data of complexes, [$^{99m}$Tc(HYNICtide)(tricine)(L)].

| Ex. # | Complex Formula | Formula Weight | Found $(M + 1)^+$ | Found $(M + 2)^{2+}$ |
|---|---|---|---|---|
| 1 | C$_{56}$H$_{77}$N$_{16}$O$_{19}$Tc | 1377.2 | 1378.3 | 689.5 |
| 3 | C$_{56}$H$_{81}$N$_{16}$O$_{20}$Tc | 1397.3 | 1398.3 | 699.2 |

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

UTILITY

The radiopharmaceuticals provided herein are useful as imaging agents for the diagnosis of cardiovascular disorders, such as thromboembolic disease or atherosclerosis, infectious disease and cancer. The radiopharmaceuticals are comprised of technetium-99m labeled hydrazino or diazenido modified biologically active molecules that selectively localize at sites of disease and thus allow an image to be obtained of the loci using gamma scintigraphy.

Canine Deep Vein Thrombosis Model:

This model incorporates the triad of events (hypercoagulatible state, period of stasis, low shear environment) essential for the formation of a venous fibrin-rich actively growing thrombus. The procedure was as follows: Adult mongrel dogs of either sex (9–13 kg) were anesthetized with pentobarbital sodium (35 mg/kg, i.v.) and ventilated with room air via an endotracheal tube (12 strokes/min, 25 ml/kg). For arterial pressure determination, the right femoral artery was cannulated with a saline-filled polyethylene catheter (PE-240) and connected to a Statham pressure transducer (P23ID; Oxnard, Calif.). Mean arterial blood pressure was determined viadamping the pulsatile pressure signal. Heart rate was monitored using a cardiotachometer (Biotach, Grass Quincy, Mass.) triggered from a lead II electrocardiogram generated by limb leads. The right femoral vein was cannulated (PE-240) for drug administration. A 5 cm segment of both jugular veins was isolated, freed from fascia and circumscribed with silk suture. A microthermister probe was placed on the vessel which serves as an indirect measure of venous flow. A balloon embolectomy catheter was utilized to induce the 15 min period of stasis during which time a hypercoagulatible state was then induced using 5 U thrombin (American Diagnosticia, Greenwich Conn.) administered into the occluded segment. Fifteen minutes later, flow was reestablished by deflating the balloon. The radiopharmaceutical was infused during the first 5 minutes of reflow and the rate of incorporation monitored using gamma scintigraphy.

Canine Arteriovenous Shunt Model:

Adult mongrel dogs of either sex (9–13 kg) were anesthetized with pentobarbital sodium (35 mg/kg, i.v.) and ventilated with room air via an endotracheal tube (12 strokes/min, 25 ml/kg). For arterial pressure determination, the left carotid artery was cannulated with a saline-filled polyethylene catheter (PE-240) and connected to a Statham pressure transducer (P23ID; Oxnard, Calif.). Mean arterial blood pressure was determined via damping the pulsatile pressure signal. Heart rate was monitored using a cardiotachometer (Biotach, Grass Quincy, Mass.) triggered from a lead II electrocardiogram generated by limb leads. A jugular vein was cannulated (PE-240) for drug administration. The both femoral arteries and femoral veins were cannulated with silicon treated (Sigmacote, Sigma Chemical Co. St Louis, Mo.), saline filled polyethylene tubing (PE-200) and connected with a 5 cm section of silicon treated tubing (PE-240) to form an extracorporeal arteriovenous shunts (A-V). Shunt patency was monitored using a doppler flow system (model VF-1, Crystal Biotech Inc, Hopkinton, Mass.) and flow probe (2–2.3 mm, Titronics Med. Inst., Iowa City, Iowa) placed proximal to the locus of the shunt. All parameters were monitored continuously on a polygraph recorder (model 7D Grass) at a paper speed of 10 mm/min or 25 mm/sec.

On completion of a 15 min post surgical stabilization period, an occlusive thrombus was formed by the introduction of a thrombogenic surface (4–0 braided silk thread, 5 cm in length, Ethicon Inc., Somerville, N.J.) into the shunt one shunt with the other serving as a control. Two consecutive 1 hr shunt periods were employed with the test agent administered as an infusion over 5 min beginning 5 min before insertion of the thrombogenic surface. At the end of each 1 hr shunt period the silk was carefully removed and weighed and the % incorporation determined via well counting. Thrombus weight was calculated by subtracting the weight of the silk prior to placement from the total weight of the silk on removal from the shunt. Arterial blood was withdrawn prior to the first shunt and every 30 min thereafter for determination of blood clearance, whole blood collagen-induced platelet aggregation, thrombin-induced platelet degranulation (platelet ATP release), prothrombin time and platelet count. Template bleeding time was also performed at 30 min intervals.

Complexes in which the biologically active molecules, Q, are chemotactic peptides can be evaluated for potential clinical utility as radiopharmaceuticals for the diagnosis of infection by performing imaging studies in a guinea pig model of focal infection.

Guinea Pig Focal Infection Model:

Hartley guinea pigs, nspecified sex, weight between 200–250 grams, are fasted overnight prior to the procedure. Each guinea pig is anesthetized with a mixture of ketamine 25-55 mg/kg//IM and xylazine 2–5 mg/kg/IM. A #10 trochar needle is used to introduce a 2 inch piece of umbilical string that has been immersed in a 6% sodium caseinate solution (this is the chemoattractant) into the right flank and is placed on the left side of the peritoneal cavity. The placement of the chemoattractant serves as a focal site for white blood cell recruitment. The puncture site is sealed with Nexabain, a skin glue (if required). The animals are allowed to recover for 18 hrs.

Eighteen hours later the guinea pigs are anesthetized with kettamine 25–55 mg/kg//IM and xylazine 2–5 mg/kg/IM to achieve Stage III/Plane III of anesthesia and insure proper injection of the test agent into the lateral saphenous vein. Once the test agent is administered the guinea pigs are placed behind a lead shield and monitored for 1–4 hours. At the appropriate time postinjection, the animals are euthanized with pentobarbital sodium 65 mg/kg, I.V. and a biodistribution performed. Throughout the course of the study, blood samples are withdrawn via cardiac puncture.

What is claimed is:

1. A radiopharmaceutical of formula (1):

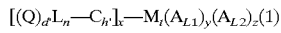

and pharmaceutically acceptable salts thereof wherein,

Q is a biologically active group;

d' is 1 to 20;

$L_n$ is a linking group of formula:

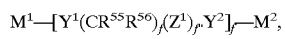

$M^1$ is $-[(CH_2)_g Z^1]_{g'}-(CR^{55}R^{56})_{g''}-$;

$M^2$ is $-(CR^{55}R^{56})_{g''}-[Z^1(CH_2)_g]_{g'}-$;

g is independently 0–10;

g' is independently 0–1;

g" is independently 0–10;

f is independently 0–10;

f is independently 0–10;

f' is independently 0–1;

$Y^1$ and $Y^2$, at each occurrence, are independently selected from: a bond, O, $NR^{56}$, C=O, C(=O)O, OC(=O)O, C(=O)NH—, C=$NR^{56}$, S, SO, $SO_2$, $SO_3$, NHC(=O), $(NH)_2C(=O)$, and $(NH)_2C=S$;

$Z^1$ is independently selected at each occurrence from a $C_6$–$C_{14}$ saturated, partially saturated, or aromatic carbocyclic ring system, substituted with 0–4 $R^{57}$; and a heterocyclic ring system, optionally substituted with 0–4 $R^{57}$;

$R^{55}$ and $R^{56}$ are independently selected at each occurrence from: H, $C_1$–$C_{10}$ alkyl substituted with 0–5 $R^{57}$, and alkaryl wherein the aryl is substituted with 0–5 $R^{57}$;

$R^{57}$ is independently selected at each occurrence from the group: H, OH, $NHR^{58}$, C(=O)$R^{58}$, OC(=O)$R^{58}$, OC(=O)O$R^{58}$, C(=O)O$R^{58}$, C(=O)N$R^{58}$, —CN, S$R^{58}$, SO$R^{58}$, $SO_2R^{58}$, NHC(=O)$R^{58}$, NHC(=O)NH$R^{58}$, and NHC(=S)NH$R^{58}$, alternatively, when attached to an additional molecule Q, $R^{57}$ is independently selected at each occurrence from the group: O, NR$^{58}$, C=O, C(=O)O, OC(=O)O, C(=O)N, C=NR$^{58}$, S, SO, SO$_2$, SO$_3$, NHC(=O), (NH)$_2$C(=O), and (NH)$_2$C=S;

R$^{58}$ is independently selected at each occurrence from the group: H, C$_1$–C$_6$ alkyl, benzyl, and phenyl;

x, y and z are independently 1 or 2;

M$_t$ is a transition metal radionuclide selected from the group: $^{99m}$Tc, $^{186}$Re and $^{188}$Re;

C$_{h'}$ is a radionuclide metal chelator coordinated to transition metal radionuclide M$_t$, and is independently selected at each occurrence, from the group: R$^{40}$N=N$^+$=, R$^{40}$R$^{41}$N—N=, and R$^{40}$N=N(H)—;

R$^{40}$ is independently selected at each occurrence from the group: a bond to L$_n$, C$_1$–C$_{10}$ alkyl substituted with 0–3 R$^{52}$, aryl substituted with 0–3 R$^{52}$, cycloaklyl substituted with 0–3 R$^{52}$, heterocycle substituted with 0–3 R$^{52}$, heterocycloalkyl substituted with 0–3 R$^{52}$, aralkyl substituted with 0–3 R$^{52}$ and alkaryl substituted with 0–3 R$^{52}$;

R$^{41}$ is independently selected from the group: H, aryl substituted with 0–3 R$^{52}$, C$_1$–C$_{10}$ alkyl substituted with 0–3 R$^{52}$, and a heterocycle substituted with 0–3 R$^{52}$;

R$^{52}$ is independently selected at each occurrence from the group: a bond to L$_n$, =O, F, Cl, Br, I, —CF$_3$, —CN, —CO$_2$R$^{53}$, —C(=O)R$^{53}$, —C(=O)N(R$^{53}$)$_2$, —CHO, —CH$_2$OR$^{53}$, —OC(=O)R$^{53}$, —OC(=O)OR$^{53a}$, —OR$^{53}$, —OC(=O)N(R$^{53}$)$_2$, —NR$^{53}$C(=O)R$^{53}$, —N(R$^{53}$)$_3^+$, —NR$^{54}$C(=O)OR$^{53a}$, —NR$^{53}$C(=O)N(R$^{53}$)$_2$, —NR$^{54}$SO$_2$N(R$^{53}$)$_2$, —NR$^{54}$SO$_2$R$^{53a}$, —SO$_3$H, —SO$_2$R$^{53a}$, —SR$^{53}$, —S(=O)R$^{53a}$, —SO$_2$N(R$^{53}$)$_2$, —N(R$^{53}$)$_2$, —NHC(=NH)NHR$^{53}$, —C(=NH)NHR$^{53}$, =NOR$^{53}$, NO$_2$, —C(=O)NHOR$^{53}$, —C(=O)NHNR$^{53}$R$^{53a}$, —OCH$_2$CO$_2$H, and 2-(1-morpholino)ethoxy;

R$^{53}$, R$^{53a}$, and R$^{54}$ are each independently selected at each occurrence from the group: H, C$_1$–C$_6$ alkyl, and a bond to L$_n$;

A$_{L1}$ is a first ancillary ligand and is a dioxygen ligand or a functionalized aminocarboxylate;

A$_{L2}$ is second ancillary ligand, capable of stabilizing the radiopharmaceutical, of the formula:

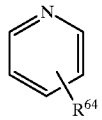

R$^{64}$ is C(O)NR$^{67}$R$^{64a}$ or C(O)OR$^{64a}$;

R$^{64a}$ is selected from the group: C$_{1-10}$ alkyl substituted with 1–5 R$^{65}$ and 0–2 R$^{65a}$, C$_{2-10}$ alkenyl substituted with 1–5 R$^{65}$ and 0–2 R$^{65a}$, C$_{2-10}$ alkynyl substituted with 1–5 R$^{65}$ and 0–2 R$^{65a}$, aryl substituted with 1–3 R$^{65}$ and 0–2 R$^{65a}$, and C$_{3-10}$ carbocycle substituted with 1–3 R$^{65}$ and 0–2 R$^{65a}$;

R$^{65}$ is independently selected at each occurrence from the group: —OR$^{66}$, —CO$_2$R$^{66}$, —OC(=O)R$^{66}$, —OC(=O)OR$^{66}$, —OCH$_2$CO$_2$R$^{66}$, —NR$^{67}$C(=O)OR$^{66}$, —SO$_2$R$^{66a}$, —NR$^{67}$SO$_2$R$^{66a}$, and PO$_3$R$^{66a}$;

R$^{65a}$ is independently selected at each occurrence from the group: =O, F, Cl, Br, I, —CF$_3$, —CN, —NO$_2$, —C(=O)R$^{66}$, —C(=O)N(R$^{66}$)$_2$, —N(R$^{66}$)$_3^+$, —OC(=O)N(R$^{66}$)$_2$, —NR$^{66}$C(=O)R$^{66}$, —NR$^{67}$C(=O)OR$^{66a}$, —NR$^{66}$C(=O)N(R$^{66}$)$_2$, —NR$^{67}$SO$_2$N(R$^{66}$)$_2$, —SO$_2$N(R$^{66}$)$_2$, and —N(R$^{66}$)$_2$;

R$^{66}$ is independently selected at each occurrence from the group: H and C$_1$–C$_6$ alkyl; R$^{66a}$ is independently selected at each occurrence from the group: H and C$_1$–C$_6$ alkyl; and, R$^{67}$ is independently selected at each occurrence from the group: H and C$_1$–C$_6$ alkyl.

2. The radiopharmaceutical of claim 1 wherein:

Q is a biologically active molecule selected from the group: IIb/IIIa receptor antagonists, IIb/IIIa receptor ligands, fibrin binding peptides, leukocyte binding peptides, chemotactic peptides, somatostatin analogs, selectin binding peptides, and vitronectin receptor antagonists;

d' is 1 to 3;

L$_n$ is:

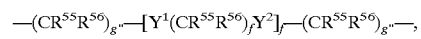

g" is 0–5;

f is 0–5;

f is 1–5;

Y$^1$ and Y$^2$, at each occurrence, are independently selected from: O, NR$^{56}$, C=O, C(=O)O, OC(=O)O, C(=O)NH, C=NR$^{56}$, S, SO, SO$_2$, SO$_3$, NHC(=O), (NH)$_2$C(=O), and (NH)$_2$C=S;

R$^{55}$ and R$^{56}$ are independently selected at each occurrence from: H, C$_1$–C$_{10}$ alkyl and alkaryl;

x and y are 1;

M$_t$ is $^{99m}$Tc;

C$_{h'}$ is R$^{40}$N=N$^+$=or R$^{40}$R$^{41}$N—N=;

R$^{40}$ is independently selected at each occurrence from the group: aryl substituted with 0–3 R$^{52}$, and heterocycle substituted with 0–3 R$^{52}$;

R$^{41}$ is independently selected from the group: H, aryl substituted with 0–1 R$^{52}$, C$_1$–C$_3$ alkyl substituted with 0–1 R$^{52}$, and a heterocycle substituted with 0–1 R$^{52}$;

R$^{52}$ is independently selected at each occurrence from the group: a bond to L$_n$, —CO$_2$R$^{53}$, —CH$_2$OR$^{53}$, —SO$_3$H, —SO$_2$R$^{53a}$, —N(R$^{53}$)$_2$, —N(R$^{53}$)$_3^+$, —NHC(=NH)NHR$^{53}$, and —OCH$_2$CO$_2$H;

R$^{53}$ and R$^{53a}$ are each independently selected at each occurrence from the group: H and C$_{1-C3}$ alkyl;

A$_{L1}$ is a functionalized aminocarboxylate;

A$_{L2}$ is second ancillary ligand, capable of stabilizing the radiopharmaceutical, of the formula:

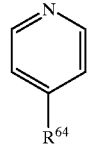

R$^{64}$ is C(O)NR$^{67}$R$^{64a}$;

R$^{64a}$ is selected from the group: C$_{1-6}$ alkyl substituted with 1–5 R$^{65}$ and 0–2 R$^{65a}$, C$_{2-6}$ alkenyl substituted with 1–5 R$^{65}$ and 0–2 R$^{65a}$, and phenyl substituted with 1–3 R$^{65}$ and 0–2 R$^{65a}$;

R$^{65}$ is independently selected at each occurrence from the group: —OR$^{66}$, —CO$_2$R$^{66}$, —OC(=O)R$^{66}$, —OC(=O)OR$^{66}$, —OCH$_2$CO$_2$R$^{66}$, —NR$^{67}$C(=O)OR$^{66}$, —SO$_2$R$^{66a}$, —NR$^{67}$SO$_2$R$^{66a}$, and —PO$_3$R$^{66a}$;

R$^{65a}$ is independently selected at each occurrence from the group: =O, F, Cl, Br, I, —CF$_3$, —CN, —NO$_2$, —C(=O)R$^{66}$, —C(=O)N(R$^{66}$)$_2$, —NR$^{66}$C(=O)R$^{66}$, —SO$_2$N(R$^{66}$)$_2$, and —N(R$^{66}$)$_2$;

R$^{66}$ is independently selected at each occurrence from the group: H and C$_1$–C$_6$ alkyl;

$R^{66a}$ is independently selected at each occurrence from the group: H and $C_1$–$C_6$ alkyl; and, $R^{67}$ is independently selected at each occurrence from the group: H and $C_1$–$C_6$ alkyl.

3. The radiopharmaceutical of claim 2 wherein:

Q is a biologically active molecule selected from the group: IIb/IIIa receptor antagonists and chemotactic peptides;

d' is 1;

$Y^1$ and $Y^2$, at each occurrence, are independently selected from: O, $NR^{56}$, C=O, C(=O)O, OC(=O)O, C(=O)NH, C=$NR^{56}$, NHC(=O), and $(NH)_2C(=O)$;

$R^{55}$ and $R^{56}$ are H;

z is 1;

$R^{40}$ is heterocycle substituted with $R^{54}$;

$R^{41}$ is H;

$R^{52}$ is a bond to $L_n$;

$A_{L1}$ is tricine;

$A_{L2}$ is second ancillary ligand, capable of stabilizing the radiopharmaceutical, of the formula:

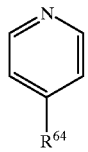

$R^{64a}$ is $C_{1-6}$ alkyl substituted with 1–5 $R^{65}$ and 0–2 $R^{65a}$;

$R^{65}$ is independently selected at each occurrence from the group: —$OR^{66}$, and —$CO_2R^{66}$;

$R^{65a}$ is independently selected at each occurrence from the group: =O, F, Cl, Br, I, —C(=O)$R^{66}$, —C(=O)N$(R^{66})_2$, —$NR^{66}$C(=O)$R^{66}$, and —N$(R^{66})_2$;

$R^{66}$ is independently selected at each occurrence from the group: H and C1-3 alkyl;

$R^{66a}$ is independently selected at each occurrence from the group: H and C1–3 alkyl; and, $R^{67}$ is independently selected at each occurrence from the group: H and $C_{1-3}$ alkyl.

4. The radiopharmaceutical of claim 3 wherein:

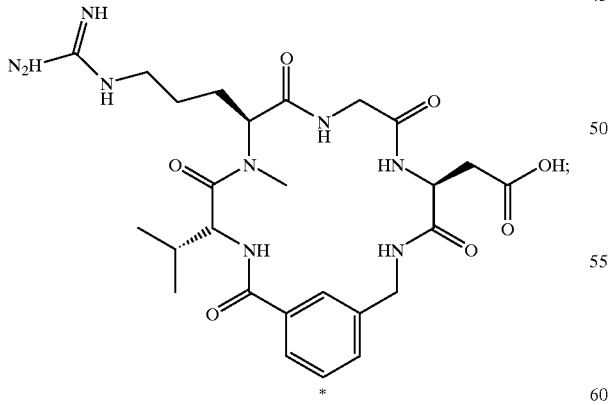

Q is d' is 1;

$L_n$ is attached to Q at the carbon atom designated with a * and has the formula:

—(C=O)NH(CH$_2$)$_5$C(=O)NH—;

$C_{h'}$ is

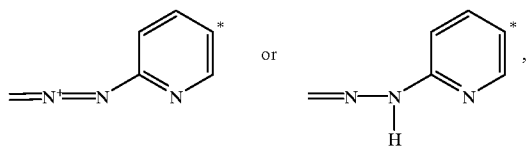

and is attached to $L_n$ at the carbon atom designated with a * $M_t$ is $^{99m}$TC;

$A_{L1}$ is tricine;

and $A_{L2}$ is selected from the group:

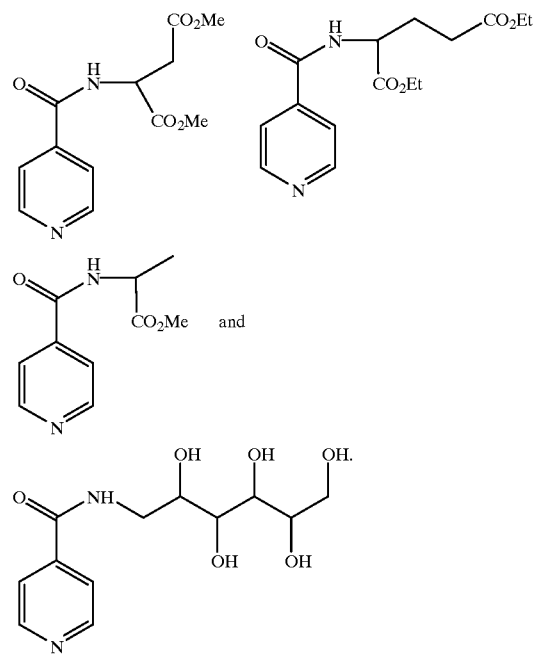

5. A radiopharmaceuitcal according to claim 1, wherin the radiopharmaceutical is selected from the group:

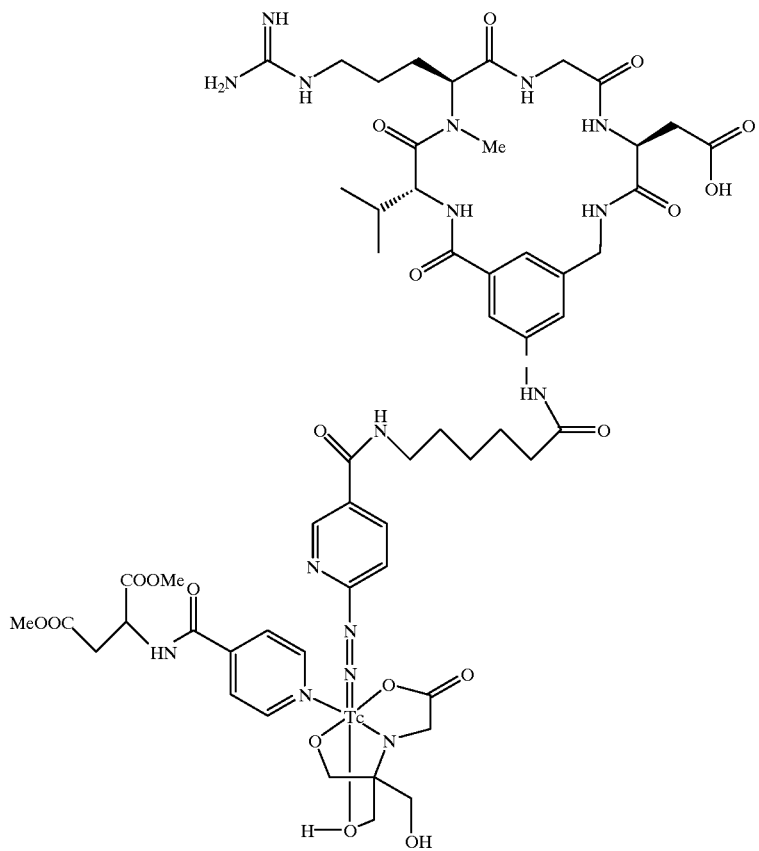
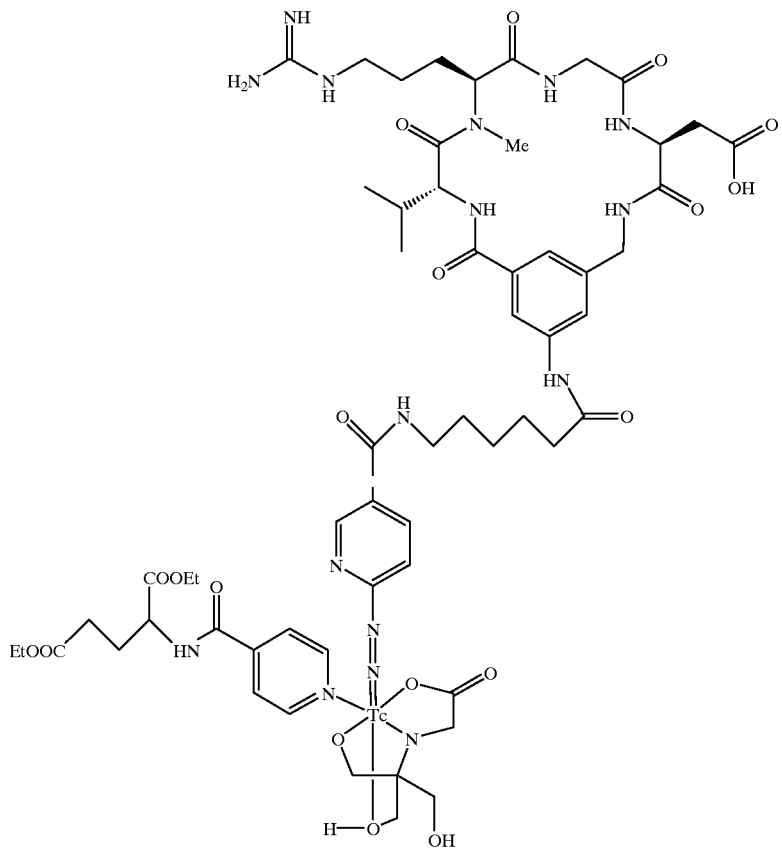

-continued
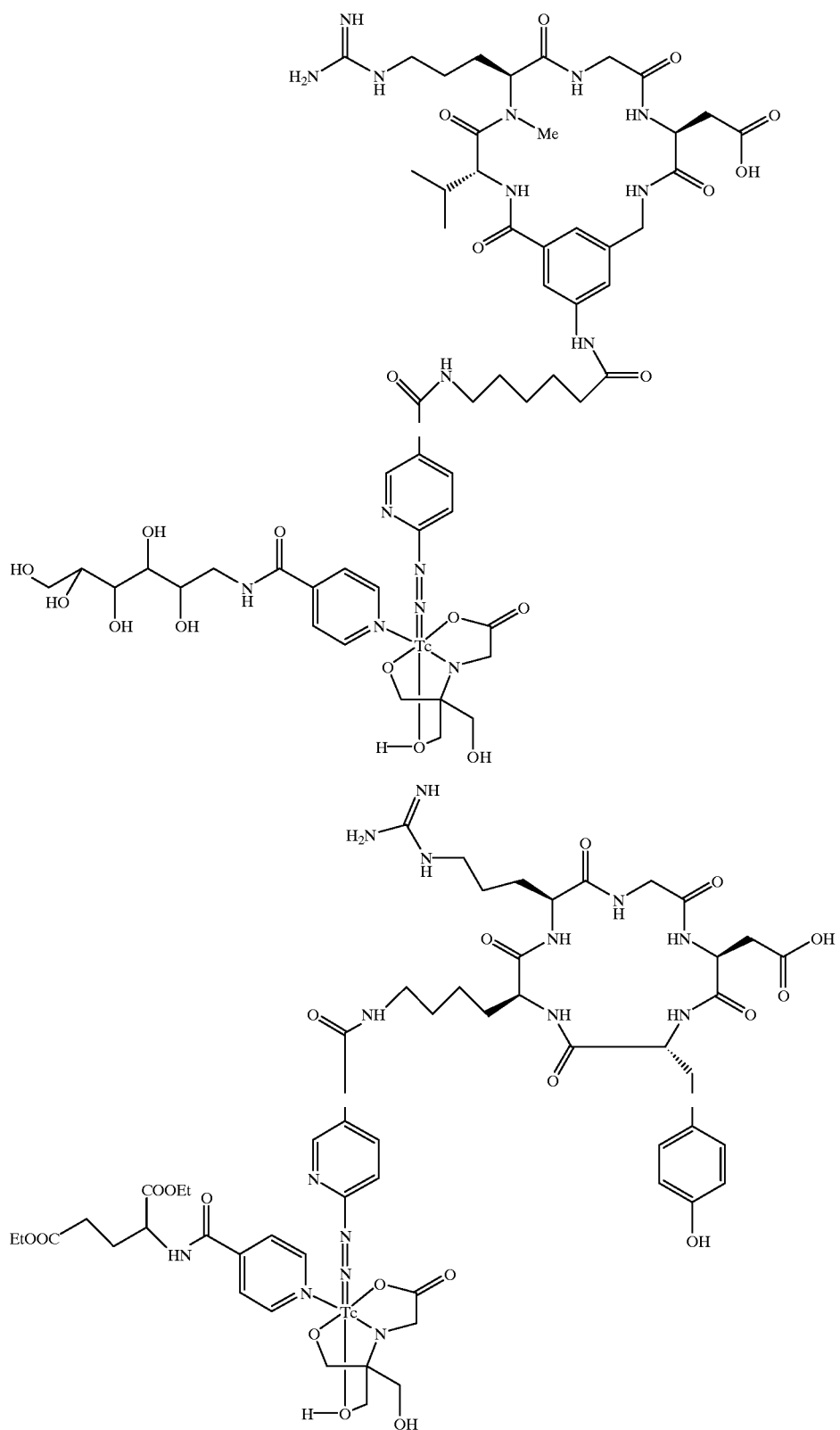

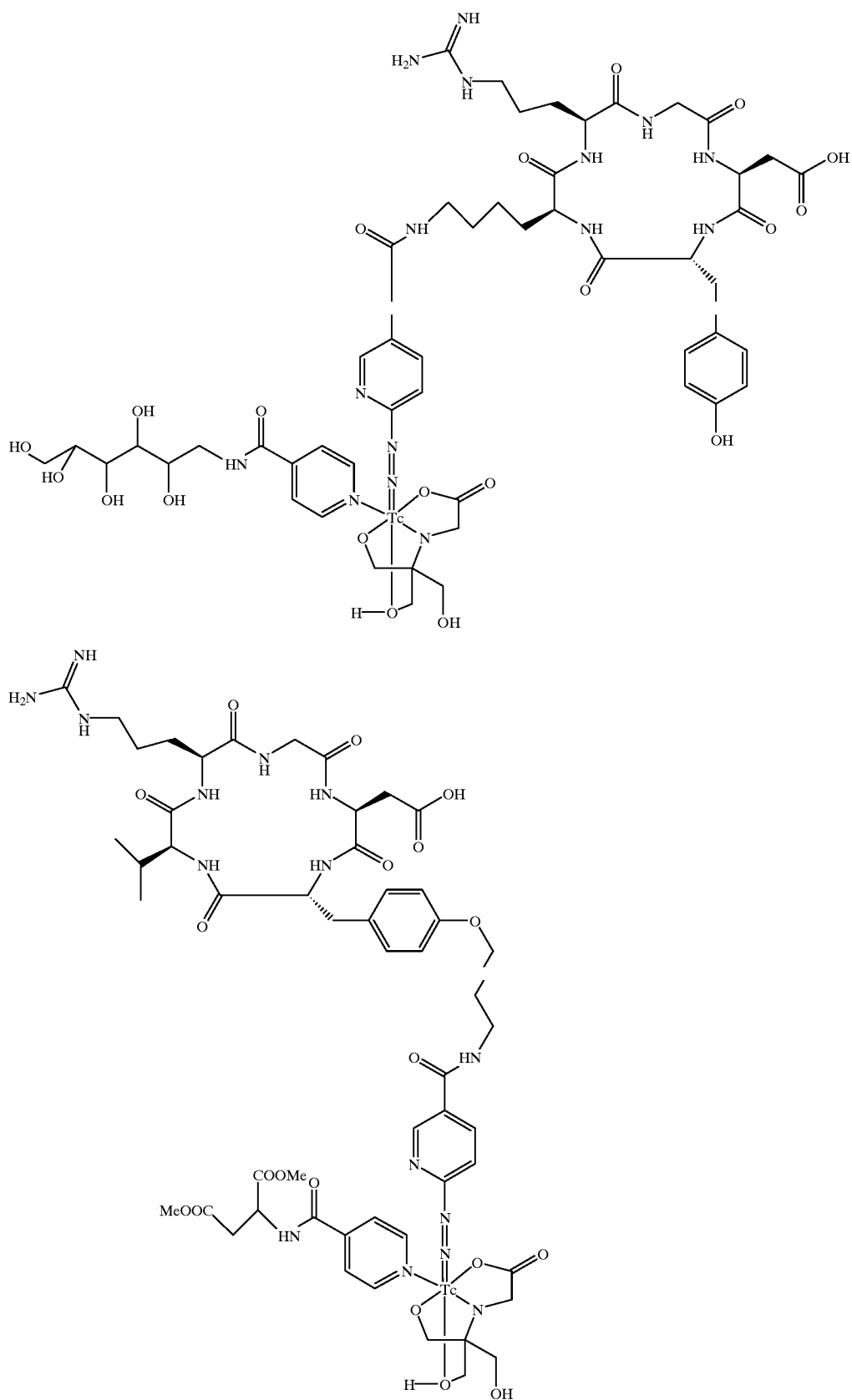

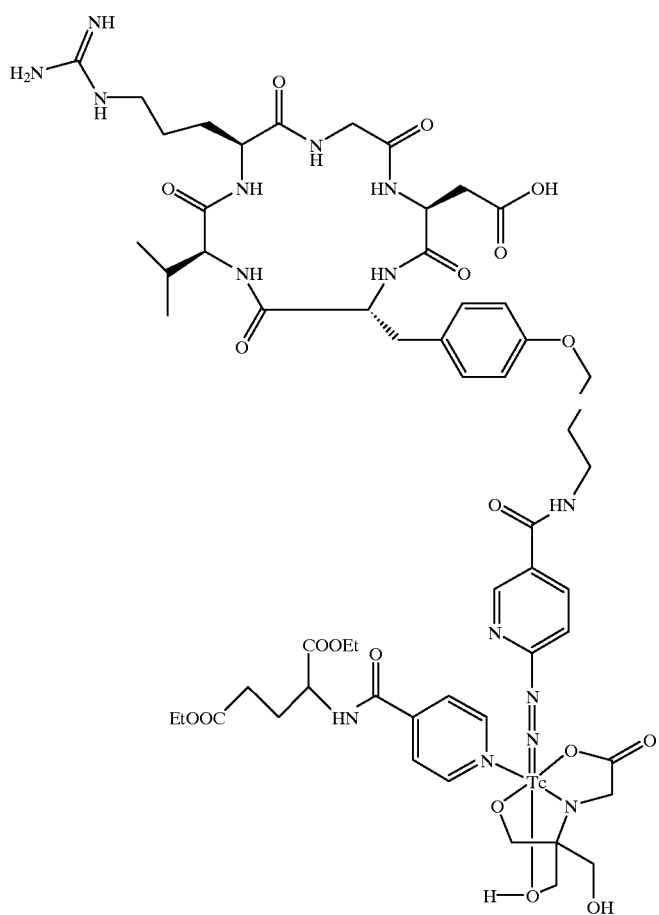
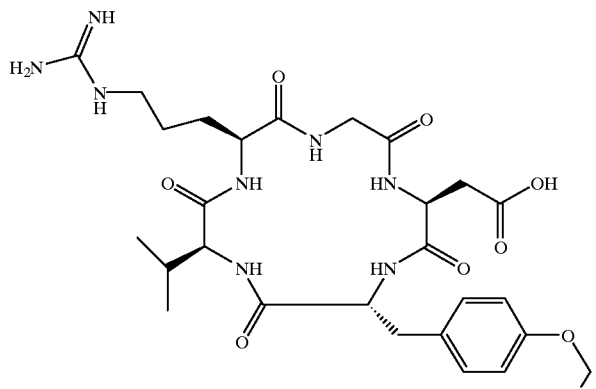

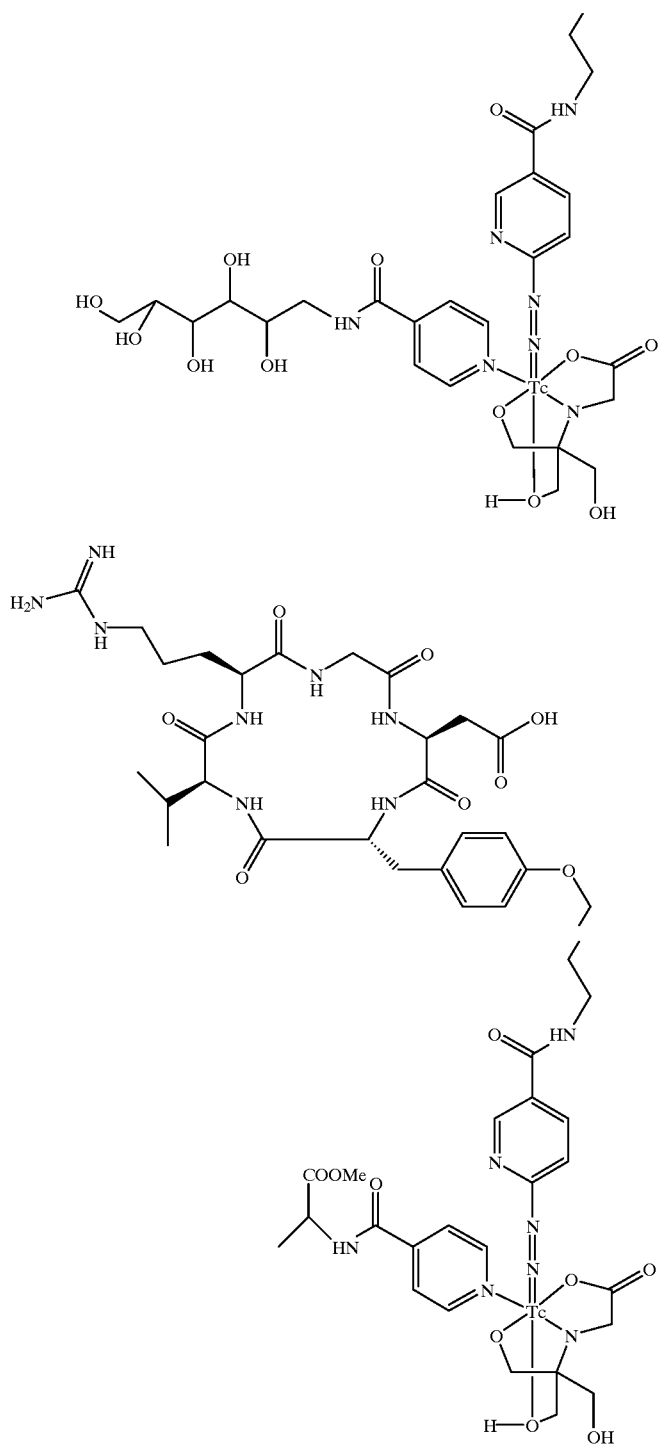

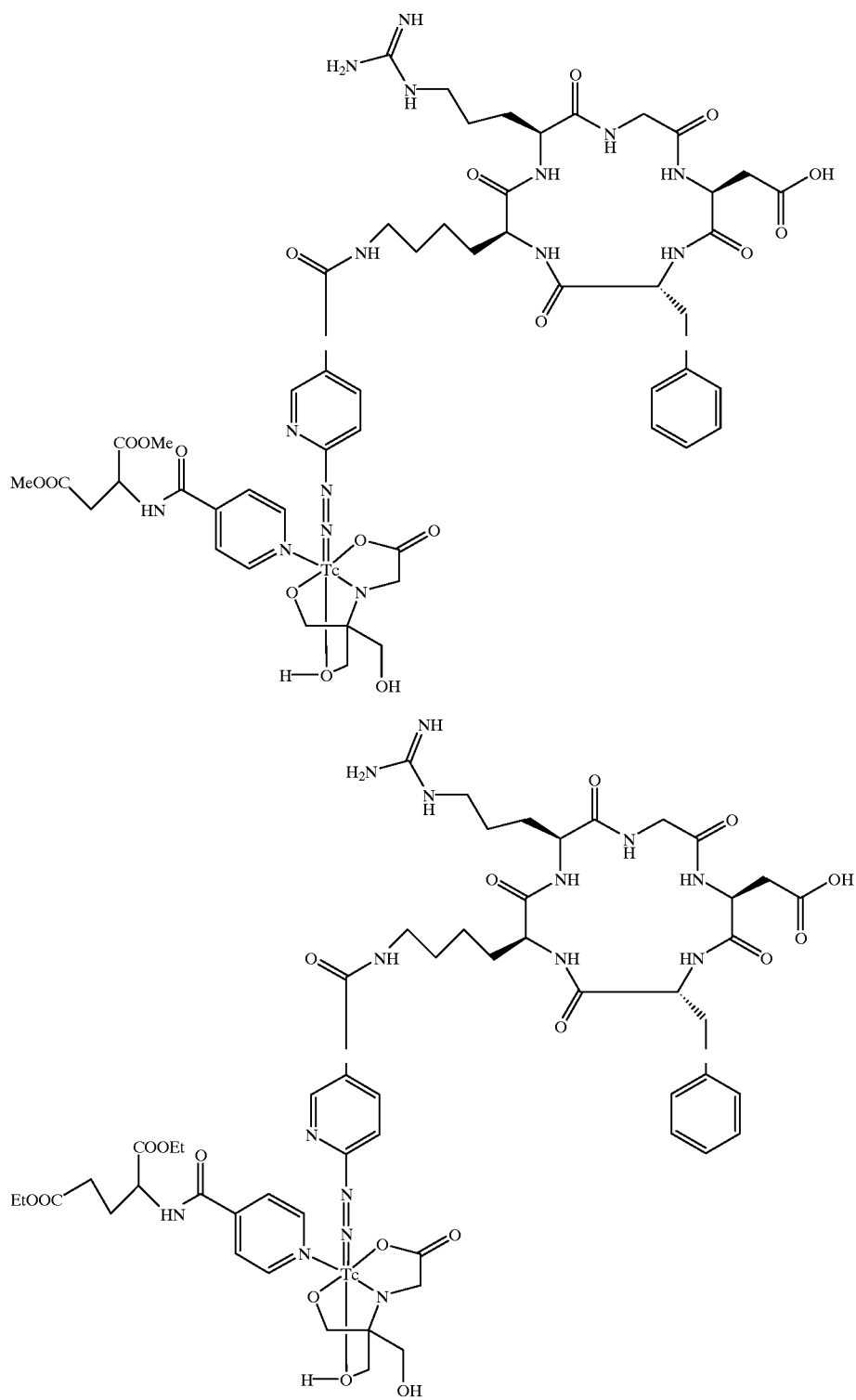

-continued

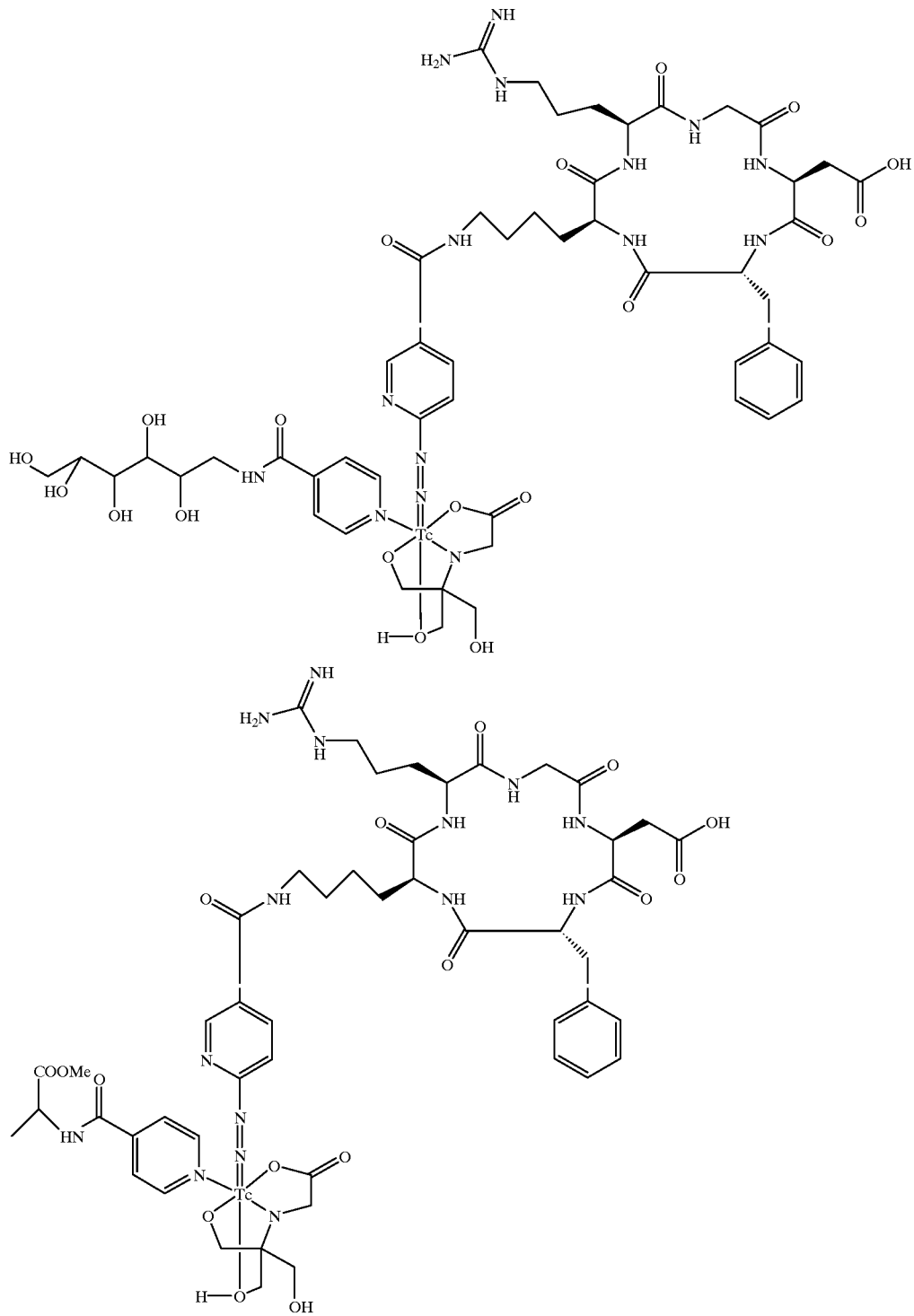

or a pharmaceutically acceptable salt form thereof.

6. A method for radioimaging a mammal comprising (i) administering to said mammal an effective amount of a radiopharmaceutical of claim 1, and (ii) scanning the mammal using a radioimaging device.

7. A method for visualizing sites of platelet deposition in a mammal by radioimaging, comprising (i) administering to said mammal an effective amount of a radiopharmaceutical of claim 1, and (ii) scanning the mammal using a radioimaging device.

8. A method of determining platelet deposition in a mammal comprising administering to said mammal a radiopharmaceutical composition of claim 1, and imaging said mammal.

9. A method of diagnosing a disorder associated with platelet deposition in a mammal comprising administering to said mammal a radiopharmaceutical composition of claim 1, and imaging said mammal.

10. A kit for preparing a radiopharmaceutical comprising:
(a) a predetermined quantity of a sterile, pharmaceutically acceptable reagent of formula:

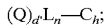

(b) a predetermined quantity of a sterile, pharmaceutically acceptable first ancillary ligand, $A_{L1}$, selected from the group: a dioxygen ligand and a functionalized aminocarboxylate;
(c) a predetermined quantity of a sterile, pharmaceutically acceptable second ancillary ligand, $A_{L2}$, of the formula:

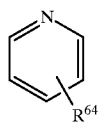

(d) a predetermined quantity of a sterile, pharmaceutically acceptable reducing agent; and
(e) optionally, a predetermined quantity of one or more sterile, pharmaceutically acceptable components selected from the group: transfer ligands, buffers, lyophilization aids, stabilization aids, solubilization aids and bacteriostats;

wherein:
Q is a biologically active molecule;
d' is 1 to 20;
$L_n$ is a linking group of formula:

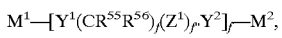

$M^1$ is $—[(CH_2)_{gZ}{}^1]_g—(CR^{55}R^{56})_{g''}—$;
$M^2$ is $—(CR^{55}R^{56})_{g''}—[Z^1(CH_2)_g]_{g'}—$;
g is independently 0–10;
g' is independently 0–1;
g" is independently 0–10;
f is independently 0–10;
f is independently 0–10;
f' is independently 0–1;
$Y^1$ and $Y^2$, at each occurrence, are independently selected from: a bond, O, $NR^{56}$, C=O, C(=O)O, OC(=O)O, C(=O)NH—, C=$NR^{56}$, S, SO, $SO_2$, $SO_3$, NHC(=O), $(NH)_2$C(=O), and $(NH)_2$C=S;
$Z^1$ is independently selected at each occurrence from a $C_6$–$C_{14}$ saturated, partially saturated, or aromatic carbocyclic ring system, substituted with 0–4 $R^{57}$; and a heterocyclic ring system, optionally substituted with 0–4 $R^{57}$;
$R^{55}$ and $R^{56}$ are independently selected at each occurrence from: H, $C_1$–$C_{10}$ alkyl substituted with 0–5 $R^{57}$, and alkaryl wherein the aryl is substituted with 0–5 $R^{57}$;
$R^{57}$ is independently selected at each occurrence from the group: H, OH, $NHR^{58}$, C(=O)$R^{58}$, OC(=O)$R^{58}$, OC(=O)O$R^{58}$, C(=O)O$R^{58}$, C(=O)$NR^{58}$, —CN, $SR^{58}$, $SOR^{58}$, $SO_2R^{58}$, NHC(=O)$R^{58}$, NHC(=O)$NHR^{58}$, and NHC(=S)$NHR^{58}$,
alternatively, when attached to an additional molecule Q, $R^{57}$ is independently selected at each occurrence from the group: O, $NR^{58}$, C=O, C(=O)O, OC(=O)O, C(=O)N, C=$NR^{58}$, S, SO, $SO_2$, $SO_3$, NHC(=O), $(NH)_2$C(=O), and $(NH)_2$C=S;
$R^{58}$ is independently selected at each occurrence from the group: H, $C_1$–$C_6$ alkyl, benzyl, and phenyl;
x, y and z are independently 1 or 2;
$M_t$ is a transition metal radionuclide selected from the group: $^{99m}$Tc, $^{186}$Re and $^{188}$Re;
$C_{h'}$ is a radionuclide metal chelator coordinated to transition metal radionuclide $M_t$, and is independently selected at each occurrence, from the group: $R^{40}$N=$N^+$=, $R^{40}R^{41}$N—N=, and $R^{40}$N=N(H)—;
$R^{40}$ is independently selected at each occurrence from the group: a bond to $L_n$, $C_1$–$C_{10}$ alkyl substituted with 0–3 $R^{52}$, aryl substituted with 0–3 $R^{52}$, cycloaklyl substituted with 0–3 $R^{52}$, heterocycle substituted with 0–3 $R^{52}$, heterocycloalkyl substituted with 0–3 $R^{52}$, aralkyl substituted with 0–3 $R^{52}$ and alkaryl substituted with 0–3 $R^{52}$;
$R^{41}$ is independently selected from the group: H, aryl substituted with 0–3 $R^{52}$, $C_1$–$C_{10}$ alkyl substituted with 0–3 $R^{52}$, and a heterocycle substituted with 0–3 $R^{52}$;
$R^{52}$ is independently selected at each occurrence from the group: a bond to Lnl, =O, F, Cl, Br, I, —$CF_3$, —CN, —$CO_2R^{53}$, —C(=O)$R^{53}$, —C(=O)N($R^{53})_2$, —CHO, —$CH_2OR^{53}$, —OC(=O)$R^{53}$, —OC(=O)O$R^{53a}$, —$OR^{53}$, —OC(=O)N($R^{53})_2$, —$NR^{53}$C(=O)$R^{53}$, —N($R^{53})_3$+, —$NR^{54}$C(=O)$R^{53a}$, —$NR^{53}$C(=O)N($R^{53})_2$, —$NR^{54}SO^2$N($R^{53})_2$, —$NR^{54}SO_2R^{53a}$, —$SO_3$H, —$SO_2R^{53a}$, —$SR^{53}$, —S(=O)$R^{53a}$, —$SO_2$N($R^{53})_2$, —N($R^{53})_2$, —NHC(=NH)$NHR^{53}$, —C(=NH)$NHR^{53}$, =$NOR^{53}$, $NO_2$, —C(=O)$NHOR^{53}$, —C(=O)$NHNR^{53}R^{53a}$, —$OCH_2CO_2$H, and 2-(1-morpholino)ethoxy;
$R^{53}$, $R^{53a}$, and $R^{54}$ are each independently selected at each occurrence from the group: H, $C_1$–$C_6$ alkyl, and a bond to $L_n$;
$R^{64}$ is C(O)$NR^{67}R^{64a}$ or C(O)O$R^{64a}$;
$R^{64a}$ is selected from the group: $C_{1-10}$ alkyl substituted with 1–5 $R^{65}$ and 0–2 $R^{65a}$, $C_{2-10}$ alkenyl substituted with 1–5 $R^{65}$ and 0–2 $R^{65a}$, $C_{2-10}$ alkynyl substituted with 1–5 $R^{65}$ and 0–2 $R^{65a}$, aryl substituted with 1–3 $R^{65}$ and 0–2 $R^{65a}$, and $C_{3-10}$ carbocycle substituted with 1–3 $R^{65}$ and 0–2 $R^{65a}$;
$R^{65}$ is independently selected at each occurrence from the group: —$OR^{66}$, —$CO_2R^{66}$, —OC(=O)$R^{66}$, —OC(=O)O$R^{66}$, —$OCH_2CO_2R^{66}$, —$NR^{67}$C(=O)O$R^{66}$, —$SO_2R^{66a}$, —$NR^{67}SO_2R^{66a}$, and —$PO_3R^{66a}$;
$R^{65a}$ is independently selected at each occurrence from the group: =O, F, Cl, Br, I, —$CF_3$, —CN, —$NO_2$, —C(=O)$R^{66}$, —C(=O)N($R^{66})_2$, —N($R^{66})_3$+, —OC(=O)N($R^{66})_2$, —$NR^{66}$C(=O)$R^{66}$, —$NR^{67}$C(=O)O$R^{66a}$, —$NR^{66}$C(=O)N($R^{66})_2$, —$NR^{67}SO_2$N($R^{66})_2$, —$SO_2$N($R^{66})_2$, and —N($R^{66})_2$;
$R^{66}$ is independently selected at each occurrence from the group: H and $C_1$–$C_6$ alkyl;
$R^{66a}$ is independently selected at each occurrence from the group: H and $C_1$–$C_6$ alkyl; and,
$R^{67}$ is independently selected at each occurrence from the group: H and $C_1$–$C_6$ alkyl.

* * * * *